United States Patent
DiPerna

(10) Patent No.: US 8,408,421 B2
(45) Date of Patent: Apr. 2, 2013

(54) FLOW REGULATING STOPCOCKS AND RELATED METHODS

(75) Inventor: Paul M DiPerna, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 1076 days.

(21) Appl. No.: 12/260,804

(22) Filed: Oct. 29, 2008

(65) Prior Publication Data

US 2010/0065578 A1 Mar. 18, 2010

Related U.S. Application Data

(60) Provisional application No. 61/097,492, filed on Sep. 16, 2008.

(51) Int. Cl.
*B67D 7/00* (2010.01)

(52) U.S. Cl. ............ 222/4; 222/57; 222/61; 222/129.2; 222/427; 222/399; 222/452; 604/150; 604/167.05; 73/19.05; 73/19.1; 73/199

(58) Field of Classification Search .................. 62/3.64, 62/174; 604/150–151, 167.05; 73/19.05–19.06, 73/19.1, 199; 222/1, 3–4, 55, 57, 61, 129.2, 222/133, 427, 395, 399, 400.7, 188, 450–453
See application file for complete search history.

(56) References Cited

U.S. PATENT DOCUMENTS

| | | | |
|---|---|---|---|
| 318,856 A | 5/1885 | Bilz | |
| 329,881 A | 11/1885 | Benton | |
| 332,402 A | 12/1885 | Leadley | |
| 596,062 A | 12/1897 | Firey | |
| 818,938 A | 4/1906 | Crane | |
| 926,092 A | 6/1909 | Bright | |
| 1,079,522 A * | 11/1913 | Smith | ............................ 222/26 |
| 1,304,036 A | 5/1919 | Eshelby | |
| 1,314,987 A * | 9/1919 | Smith | ............................ 222/48 |
| 1,643,021 A | 9/1927 | Luyties | |
| 1,657,663 A | 6/1928 | Devereux | |
| 1,910,032 A | 5/1933 | Mills | |
| 2,018,316 A | 10/1935 | Ownings | |

(Continued)

FOREIGN PATENT DOCUMENTS

| | | |
|---|---|---|
| CN | 1229347 A | 9/1999 |
| CN | 2668155 Y | 1/2005 |

(Continued)

OTHER PUBLICATIONS

U.S. Appl. No. 60/789,243, filed Apr. 5, 2006, Beavis.

(Continued)

*Primary Examiner* — Kevin P Shaver
*Assistant Examiner* — Andrew P Bainbridge
(74) *Attorney, Agent, or Firm* — Patterson Thuente Pedersen, P.A.

(57) ABSTRACT

A dispenser using a stopcock valve has a first and second chamber. The first chamber has a flow material and is pressurized with air. The first chamber is connected to a stopcock valve that holds a second chamber which has a pressure sensor when the stopcock valve is rotated to the proper orientation. The stopcock valve is then rotated to a dispensing position where the flow material is dispensed under pressure to an outlet. By using the air pressure sensor and by taking into consideration the volume of the second chamber, the amount of flow of material can be dosed out consistently.

9 Claims, 4 Drawing Sheets

U.S. PATENT DOCUMENTS

| | | | |
|---|---|---|---|
| 2,029,630 A | 2/1936 | McMichael | |
| 2,147,164 A | 2/1939 | Kent | |
| 2,398,234 A * | 4/1946 | Long | 222/424 |
| 2,444,677 A | 7/1948 | Rosenblum | |
| 2,454,929 A | 11/1948 | Kempton | |
| 2,495,693 A | 1/1950 | Byrd, Jr. et al. | |
| 2,497,020 A | 2/1950 | Singer | |
| 2,568,519 A | 9/1951 | Smith | |
| 2,599,325 A | 6/1952 | Fritzberg | |
| 2,629,402 A | 2/1953 | Cook | |
| 2,667,900 A | 2/1954 | Cantalupo | |
| 2,674,262 A | 4/1954 | Bradshaw | |
| 2,679,954 A | 6/1954 | Barnes | |
| 2,701,583 A | 2/1955 | Rux | |
| 2,706,612 A | 4/1955 | Ratelband | |
| 2,728,355 A | 12/1955 | Dahl | |
| 2,735,642 A | 2/1956 | Norman | |
| 2,736,463 A * | 2/1956 | Levine | 222/26 |
| 2,746,709 A | 5/1956 | Minor | |
| 2,764,183 A | 9/1956 | Gollehon | |
| 2,781,058 A | 2/1957 | Warhus | |
| 2,834,379 A | 5/1958 | Fields | |
| 2,841,237 A | 7/1958 | Slayter | |
| 2,852,033 A | 9/1958 | Orser | |
| 2,878,836 A | 3/1959 | Binks | |
| 2,891,578 A | 6/1959 | Dahl et al. | |
| 2,898,078 A | 8/1959 | Stephenson et al. | |
| 2,898,088 A | 8/1959 | Alder | |
| 2,899,979 A | 8/1959 | Dahl et al. | |
| 2,936,788 A | 5/1960 | Dahl et al. | |
| 2,939,487 A | 6/1960 | Fraser et al. | |
| 2,960,109 A | 11/1960 | Wilson | |
| 2,968,318 A | 1/1961 | Bauman | |
| 2,989,086 A | 6/1961 | Dahl | |
| 3,017,903 A | 1/1962 | Steffens | |
| 3,035,613 A | 5/1962 | Beatty | |
| 3,060,966 A | 10/1962 | Ratelband | |
| 3,061,039 A | 10/1962 | Peters | |
| 3,070,132 A | 12/1962 | Sheridan | |
| 3,072,151 A | 1/1963 | Quercia | |
| 3,077,903 A | 2/1963 | Honsinger | |
| 3,095,120 A | 6/1963 | Steiner et al. | |
| 3,095,175 A | 6/1963 | Iketani | |
| 3,118,646 A | 1/1964 | Markey | |
| 3,121,445 A | 2/1964 | Wisniewski | |
| 3,123,900 A | 3/1964 | Millar | |
| 3,133,678 A * | 5/1964 | Marwell et al. | 222/204 |
| 3,143,861 A | 8/1964 | Dumas | |
| 3,174,694 A | 3/1965 | Kitabayshi | |
| 3,189,125 A | 6/1965 | Windsor et al. | |
| 3,195,586 A | 7/1965 | Vogt | |
| 3,203,662 A | 8/1965 | Lau | |
| 3,214,903 A | 11/1965 | Cochran | |
| 3,216,451 A | 11/1965 | Smallpeice | |
| 3,227,311 A * | 1/1966 | Rowell | 222/52 |
| 3,298,394 A | 1/1967 | Chorkey | |
| 3,338,049 A | 8/1967 | Fernberger | |
| 3,347,418 A * | 10/1967 | Fefferman | 222/61 |
| 3,376,625 A | 4/1968 | McCulloch | |
| 3,409,050 A | 11/1968 | Weese | |
| 3,428,223 A | 2/1969 | Lewiecki et al. | |
| 3,430,659 A | 3/1969 | Henderson | |
| 3,479,002 A | 11/1969 | Hirs | |
| 3,493,496 A | 2/1970 | Bray et al. | |
| 3,508,587 A | 4/1970 | Mauch | |
| 3,532,125 A | 10/1970 | Everett et al. | |
| 3,556,159 A | 1/1971 | Bleasdale | |
| 3,568,847 A | 3/1971 | Carr | |
| 3,583,603 A * | 6/1971 | Freckmann et al. | 222/137 |
| 3,586,040 A | 6/1971 | Urback | |
| 3,620,500 A | 11/1971 | Santomieri | |
| 3,621,882 A | 11/1971 | Kuplec | |
| 3,648,694 A * | 3/1972 | Mogos et al. | 604/118 |
| 3,654,959 A * | 4/1972 | Kassel | 137/605 |
| 3,665,967 A | 5/1972 | Kachnik | |
| 3,673,853 A * | 7/1972 | Griswold et al. | 73/19.1 |
| 3,674,183 A | 7/1972 | Venable et al. | |
| 3,675,672 A | 7/1972 | Freeman | |
| 3,693,484 A | 9/1972 | Sanderson, Jr. | |
| 3,696,958 A | 10/1972 | Lee | |
| 3,699,812 A | 10/1972 | Masnik | |
| 3,717,174 A | 2/1973 | Dewall | |
| 3,724,234 A * | 4/1973 | Garavelli | 62/308 |
| 3,756,459 A | 9/1973 | Bannister et al. | |
| 3,833,019 A | 9/1974 | Diggs | |
| 3,836,113 A | 9/1974 | Johnson | |
| 3,837,363 A | 9/1974 | Meronek | |
| 3,847,178 A | 11/1974 | Keppel | |
| 3,860,353 A | 1/1975 | Lukasik et al. | |
| 3,894,538 A | 7/1975 | Richter | |
| 3,899,135 A | 8/1975 | O'Brian | |
| 3,918,674 A | 11/1975 | Sutter | |
| 3,946,761 A | 3/1976 | Thompson et al. | |
| RE28,890 E | 7/1976 | Ingram et al. | |
| 3,970,105 A | 7/1976 | Pelton et al. | |
| 3,991,972 A | 11/1976 | Eaton | |
| 4,000,857 A | 1/1977 | Moen | |
| 4,003,398 A | 1/1977 | Duveau | |
| 4,023,772 A | 5/1977 | Ratelband | |
| 4,032,265 A | 6/1977 | Miller | |
| 4,076,872 A | 2/1978 | Lewicki et al. | |
| 4,087,301 A | 5/1978 | Steadman | |
| 4,089,206 A * | 5/1978 | Raffel et al. | 73/19.1 |
| 4,103,689 A | 8/1978 | Leighton | |
| 4,105,050 A | 8/1978 | Hendrickson et al. | |
| 4,106,510 A | 8/1978 | Hakim et al. | |
| 4,111,391 A | 9/1978 | Pilolla | |
| 4,156,127 A | 5/1979 | Sako et al. | |
| 4,178,938 A | 12/1979 | Au | |
| 4,191,184 A | 3/1980 | Carlisle | |
| 4,191,204 A | 3/1980 | Nehring | |
| 4,191,358 A | 3/1980 | Ferri | |
| 4,193,552 A | 3/1980 | Ishikawa | |
| 4,195,810 A | 4/1980 | Lavin | |
| 4,215,726 A | 8/1980 | Tagami | |
| 4,228,956 A | 10/1980 | Varner | |
| 4,248,270 A | 2/1981 | Ostrowski | |
| 4,250,872 A | 2/1981 | Tamari | |
| 4,254,791 A | 3/1981 | Bron | |
| 4,265,241 A | 5/1981 | Portner et al. | |
| 4,275,727 A | 6/1981 | Keeri-Szanto | |
| 4,314,621 A | 2/1982 | Hansen | |
| 4,327,845 A * | 5/1982 | Keyes et al. | 222/340 |
| 4,344,459 A | 8/1982 | Nelson | |
| 4,356,935 A | 11/1982 | Kamin | |
| 4,367,786 A | 1/1983 | Hafner et al. | |
| 4,382,453 A | 5/1983 | Bujan et al. | |
| 4,406,656 A | 9/1983 | Hattler et al. | |
| 4,432,468 A | 2/1984 | Siff et al. | |
| 4,440,154 A | 4/1984 | Bellows | |
| 4,443,218 A | 4/1984 | DeCant, Jr. et al. | |
| 4,448,538 A | 5/1984 | Mantel | |
| 4,457,343 A | 7/1984 | Zukausky | |
| 4,469,481 A | 9/1984 | Kobayashi | |
| 4,492,339 A | 1/1985 | Kreitzberg | |
| 4,498,843 A | 2/1985 | Schneider et al. | |
| 4,508,144 A | 4/1985 | Bernett | |
| 4,515,536 A | 5/1985 | van Os | |
| 4,527,595 A | 7/1985 | Jorgensen et al. | |
| 4,529,401 A | 7/1985 | Leslie et al. | |
| 4,557,726 A | 12/1985 | Reinicke | |
| 4,559,036 A | 12/1985 | Wunsch | |
| 4,562,960 A | 1/1986 | Marty et al. | |
| 4,570,745 A | 2/1986 | Sparks et al. | |
| 4,592,390 A | 6/1986 | Boyd | |
| 4,609,014 A | 9/1986 | Jurevic et al. | |
| 4,620,648 A | 11/1986 | Schwartzman | |
| 4,624,661 A | 11/1986 | Airmond | |
| 4,627,573 A | 12/1986 | Havens et al. | |
| 4,628,928 A | 12/1986 | Lowell | |
| 4,636,226 A | 1/1987 | Canfora | |
| 4,646,945 A | 3/1987 | Steiner et al. | |
| 4,649,959 A | 3/1987 | Wadleigh | |
| 4,650,471 A | 3/1987 | Tamari | |
| 4,651,781 A | 3/1987 | Kandelman | |
| 4,657,486 A | 4/1987 | Stempfle et al. | |
| 4,666,430 A | 5/1987 | Brown et al. | |

| Patent | Date | Inventor |
|---|---|---|
| 4,667,700 A | 5/1987 | Buzzi |
| 4,673,415 A | 6/1987 | Stanford |
| 4,684,364 A | 8/1987 | Sawyer et al. |
| 4,684,367 A | 8/1987 | Schaffer et al. |
| 4,687,423 A | 8/1987 | Maget |
| 4,713,063 A | 12/1987 | Krumme |
| 4,718,893 A | 1/1988 | Dorman et al. |
| 4,724,870 A | 2/1988 | Molb et al. |
| 4,770,211 A | 9/1988 | Olsson |
| 4,773,448 A | 9/1988 | Francis |
| 4,776,842 A | 10/1988 | Franetzki et al. |
| 4,778,451 A | 10/1988 | Kamen |
| 4,779,762 A * | 10/1988 | Klein et al. .................. 222/52 |
| 4,787,408 A | 11/1988 | Twerdochlib |
| 4,823,844 A | 4/1989 | Bartholomew |
| 4,826,482 A | 5/1989 | Kamen |
| 4,840,191 A | 6/1989 | Gausman et al. |
| 4,869,431 A | 9/1989 | Jubert et al. |
| 4,871,093 A | 10/1989 | Burshtain et al. |
| 4,883,093 A | 11/1989 | Miles et al. |
| 4,886,514 A | 12/1989 | Maget |
| 4,897,906 A | 2/1990 | Bartholomew |
| 4,902,278 A | 2/1990 | Maget et al. |
| 4,931,050 A | 6/1990 | Idriss |
| 4,938,259 A | 7/1990 | Schmidt |
| 4,955,860 A | 9/1990 | Ruano |
| 4,969,884 A | 11/1990 | Yum |
| 4,973,402 A | 11/1990 | Johnson et al. |
| 4,976,162 A * | 12/1990 | Kamen .................. 73/865.9 |
| 4,985,015 A | 1/1991 | Obermann et al. |
| 4,986,312 A | 1/1991 | Gute |
| 4,989,456 A | 2/1991 | Stupecky |
| 4,995,258 A | 2/1991 | Frank |
| 5,000,739 A | 3/1991 | Kulisz et al. |
| 5,002,527 A | 3/1991 | Reller et al. |
| 5,006,997 A | 4/1991 | Reich |
| 5,011,477 A | 4/1991 | Winchell et al. |
| 5,027,861 A | 7/1991 | Gute |
| 5,035,865 A | 7/1991 | Inaba et al. |
| 5,038,821 A | 8/1991 | Maget |
| 5,044,900 A | 9/1991 | Cavallaro |
| 5,047,044 A | 9/1991 | Smith et al. |
| 5,049,141 A | 9/1991 | Olive |
| 5,050,612 A | 9/1991 | Matsumura |
| 5,053,001 A | 10/1991 | Reller et al. |
| 5,053,189 A | 10/1991 | Chrise et al. |
| 5,059,182 A | 10/1991 | Laing |
| 5,062,834 A | 11/1991 | Gross et al. |
| 5,062,841 A | 11/1991 | Siegel |
| 5,076,911 A | 12/1991 | Brown et al. |
| 5,078,683 A | 1/1992 | Sancoff et al. |
| 5,082,240 A | 1/1992 | Richmond |
| 5,082,503 A | 1/1992 | Sluga et al. |
| 5,083,908 A | 1/1992 | Gagnebin et al. |
| 5,084,021 A | 1/1992 | Baldwin |
| 5,085,644 A | 2/1992 | Watson et al. |
| 5,087,245 A | 2/1992 | Daon |
| 5,090,963 A | 2/1992 | Gross et al. |
| 5,091,091 A | 2/1992 | Terman |
| 5,091,094 A | 2/1992 | Veech |
| 5,103,211 A | 4/1992 | Daoud et al. |
| 5,104,526 A | 4/1992 | Brown et al. |
| 5,108,363 A | 4/1992 | Tuttle et al. |
| 5,125,781 A | 6/1992 | Breunig et al. |
| 5,126,324 A | 6/1992 | Clark et al. |
| 5,127,258 A | 7/1992 | Brown et al. |
| 5,128,145 A | 7/1992 | Edgren et al. |
| 5,135,491 A | 8/1992 | Baldwin |
| 5,135,498 A | 8/1992 | Kam et al. |
| 5,135,499 A | 8/1992 | Tafani et al. |
| 5,149,413 A | 9/1992 | Maget |
| 5,154,712 A | 10/1992 | Herwick et al. |
| 5,156,591 A | 10/1992 | Gross et al. |
| 5,156,598 A | 10/1992 | Skakoon et al. |
| 5,157,960 A | 10/1992 | Brehm et al. |
| 5,158,230 A | 10/1992 | Curran |
| 5,173,302 A | 12/1992 | Holmblad et al. |
| 5,176,502 A | 1/1993 | Sanderson et al. |
| 5,178,603 A | 1/1993 | Prince |
| 5,182,258 A | 1/1993 | Chiou |
| 5,184,359 A | 2/1993 | Tsukamura et al. |
| 5,186,431 A | 2/1993 | Tamari |
| 5,186,805 A | 2/1993 | Gross et al. |
| 5,188,258 A * | 2/1993 | Iwashita .................. 222/61 |
| 5,190,522 A | 3/1993 | Wojcicki et al. |
| 5,191,719 A | 3/1993 | Kitt |
| 5,192,264 A | 3/1993 | Fossel |
| 5,203,506 A | 4/1993 | Gross et al. |
| 5,207,642 A | 5/1993 | Orkin et al. |
| 5,207,645 A | 5/1993 | Ross et al. |
| 5,207,666 A | 5/1993 | Idriss et al. |
| 5,209,265 A | 5/1993 | Taguri et al. |
| 5,215,450 A | 6/1993 | Tamari |
| 5,217,440 A | 6/1993 | Frassica |
| 5,218,987 A | 6/1993 | Heil |
| 5,220,515 A | 6/1993 | Freerks et al. |
| 5,224,796 A | 7/1993 | Zeman |
| 5,226,446 A | 7/1993 | Cooper |
| 5,228,291 A | 7/1993 | Meyering |
| 5,228,842 A | 7/1993 | Guebeli et al. |
| 5,232,437 A | 8/1993 | Lysaght et al. |
| 5,232,449 A | 8/1993 | Stern et al. |
| 5,240,603 A | 8/1993 | Frank et al. |
| 5,241,935 A | 9/1993 | Beck et al. |
| 5,242,406 A | 9/1993 | Gross et al. |
| 5,242,408 A | 9/1993 | Jhuboo et al. |
| 5,243,983 A | 9/1993 | Tarr et al. |
| 5,246,147 A | 9/1993 | Gross |
| 5,254,096 A | 10/1993 | Rondelet et al. |
| 5,257,971 A | 11/1993 | Lord et al. |
| 5,259,399 A | 11/1993 | Brown |
| 5,259,732 A | 11/1993 | Stern |
| 5,261,459 A | 11/1993 | Atkinson et al. |
| 5,261,884 A | 11/1993 | Stern et al. |
| 5,266,265 A | 11/1993 | Raible |
| 5,270,005 A | 12/1993 | Raible |
| 5,271,724 A | 12/1993 | vanLintel |
| 5,272,294 A | 12/1993 | Charboneau et al. |
| 5,272,909 A | 12/1993 | Nguyen et al. |
| 5,273,406 A | 12/1993 | Feygin |
| 5,273,518 A | 12/1993 | Lee et al. |
| 5,278,142 A | 1/1994 | Chiou |
| 5,279,543 A | 1/1994 | Glikfeld et al. |
| 5,279,586 A | 1/1994 | Balkwell |
| 5,290,684 A | 3/1994 | Kelly |
| 5,295,966 A | 3/1994 | Stern et al. |
| 5,295,967 A | 3/1994 | Rondelet et al. |
| 5,303,843 A | 4/1994 | Zink et al. |
| 5,304,126 A | 4/1994 | Epstein et al. |
| 5,304,163 A | 4/1994 | Bonnici et al. |
| 5,312,233 A | 5/1994 | Tanny et al. |
| 5,320,250 A | 6/1994 | La et al. |
| 5,321,392 A | 6/1994 | Skakoon et al. |
| 5,322,418 A | 6/1994 | Comer |
| 5,322,620 A | 6/1994 | Brown et al. |
| 5,322,626 A | 6/1994 | Frank et al. |
| 5,327,777 A | 7/1994 | Kaye et al. |
| 5,334,162 A | 8/1994 | Harris |
| 5,335,705 A * | 8/1994 | Morishita et al. ............. 141/275 |
| 5,335,852 A | 8/1994 | Muntean et al. |
| 5,336,051 A | 8/1994 | Tamari |
| 5,338,157 A | 8/1994 | Blomquist |
| 5,339,865 A | 8/1994 | Asghar et al. |
| 5,341,783 A | 8/1994 | Beck et al. |
| 5,345,488 A | 9/1994 | Skipper et al. |
| 5,348,197 A | 9/1994 | Mizzi et al. |
| 5,349,933 A | 9/1994 | Hasegawa et al. |
| 5,350,224 A | 9/1994 | Nell et al. |
| 5,352,201 A | 10/1994 | Jemmott |
| 5,354,273 A | 10/1994 | Hagen |
| 5,356,375 A | 10/1994 | Higley et al. |
| 5,356,378 A | 10/1994 | Doan |
| 5,356,632 A | 10/1994 | Gross et al. |
| 5,358,635 A | 10/1994 | Frank et al. |
| 5,360,062 A | 11/1994 | White |
| 5,360,734 A | 11/1994 | Chapman et al. |
| 5,362,307 A | 11/1994 | Guy et al. |
| 5,366,904 A | 11/1994 | Quereshi et al. |

| | | |
|---|---|---|
| 5,367,910 A | 11/1994 | Woodward |
| 5,368,555 A | 11/1994 | Sussman et al. |
| 5,369,976 A | 12/1994 | Ratton |
| 5,370,622 A | 12/1994 | Livingston et al. |
| 5,370,870 A | 12/1994 | Wong |
| 5,373,865 A | 12/1994 | Jung et al. |
| 5,381,823 A | 1/1995 | DiBartolo |
| 5,384,709 A | 1/1995 | Seder et al. |
| 5,387,327 A | 2/1995 | Khan |
| 5,388,453 A | 2/1995 | Ratton et al. |
| 5,389,078 A | 2/1995 | Zalesky et al. |
| 5,389,091 A | 2/1995 | Moorehead |
| 5,395,324 A | 3/1995 | Hinrichs |
| 5,399,166 A | 3/1995 | Laing |
| 5,403,551 A | 4/1995 | Galloway et al. |
| 5,407,444 A | 4/1995 | Kroll |
| 5,410,908 A | 5/1995 | Erichsen |
| 5,411,685 A | 5/1995 | Burgis |
| 5,415,024 A | 5/1995 | Proffitt et al. |
| 5,418,154 A | 5/1995 | Aebischer et al. |
| 5,421,208 A | 6/1995 | Packard et al. |
| 5,423,743 A | 6/1995 | Buttrefield |
| 5,425,374 A | 6/1995 | Ueda et al. |
| 5,425,706 A | 6/1995 | Gross et al. |
| 5,425,742 A | 6/1995 | Joy |
| 5,427,870 A | 6/1995 | Joshi et al. |
| 5,429,483 A | 7/1995 | Tamari |
| 5,429,601 A | 7/1995 | Conley et al. |
| 5,431,171 A | 7/1995 | Harrison et al. |
| 5,433,710 A | 7/1995 | VanAntwerp et al. |
| 5,435,465 A | 7/1995 | El-Amin |
| 5,435,697 A | 7/1995 | Guebeli et al. |
| 5,435,797 A | 7/1995 | Harris |
| 5,438,510 A | 8/1995 | Bryant et al. |
| 5,441,027 A | 8/1995 | Buchanon et al. |
| 5,442,948 A | 8/1995 | Cowing |
| 5,442,950 A | 8/1995 | Unalmiser et al. |
| 5,443,450 A | 8/1995 | Kratoska |
| 5,445,616 A | 8/1995 | Kratoska et al. |
| 5,447,509 A | 9/1995 | Mills et al. |
| 5,447,863 A | 9/1995 | Langley |
| 5,448,034 A | 9/1995 | Skipper et al. |
| 5,448,978 A | 9/1995 | Hasegawa et al. |
| 5,450,750 A | 9/1995 | Abler |
| 5,454,922 A | 10/1995 | Joshi et al. |
| 5,458,469 A | 10/1995 | Hauser |
| 5,460,030 A | 10/1995 | Blosxom et al. |
| 5,460,605 A | 10/1995 | tuttle et al. |
| 5,460,945 A | 10/1995 | Springer et al. |
| 5,462,525 A | 10/1995 | Srisathapat et al. |
| 5,462,535 A | 10/1995 | Bonnichsen et al. |
| 5,464,392 A | 11/1995 | Epstein et al. |
| 5,464,398 A | 11/1995 | Haindl |
| 5,466,218 A | 11/1995 | Srisathapat et al. |
| 5,466,229 A | 11/1995 | Elson et al. |
| 5,469,846 A | 11/1995 | Khan |
| 5,470,318 A | 11/1995 | Griffith, III et al. |
| 5,472,577 A | 12/1995 | Porter et al. |
| 5,476,444 A | 12/1995 | Keeling et al. |
| 5,476,449 A | 12/1995 | Richmond |
| 5,478,751 A | 12/1995 | Oosta et al. |
| 5,480,381 A | 1/1996 | Weston |
| 5,482,745 A | 1/1996 | Cuellar et al. |
| 5,483,930 A | 1/1996 | Moriya et al. |
| 5,485,408 A | 1/1996 | Blomquist |
| 5,487,528 A | 1/1996 | Richmond |
| 5,489,265 A | 2/1996 | Montalvo et al. |
| 5,492,534 A | 2/1996 | Athayde et al. |
| 5,494,578 A | 2/1996 | Brown et al. |
| 5,498,421 A | 3/1996 | Grinstaff et al. |
| 5,503,538 A | 4/1996 | Wiernicki et al. |
| 5,505,709 A | 4/1996 | Funderburk et al. |
| 5,505,777 A | 4/1996 | Ciardella et al. |
| 5,509,294 A | 4/1996 | Gowing |
| 5,510,336 A | 4/1996 | Saven et al. |
| 5,518,730 A | 5/1996 | Fuisz |
| 5,526,675 A | 6/1996 | Ratton |
| 5,527,288 A | 6/1996 | Gross et al. |
| 5,527,307 A | 6/1996 | Srisathapat et al. |
| 5,527,704 A | 6/1996 | Wolf, Jr. et al. |
| 5,533,876 A | 7/1996 | Nelson, II |
| 5,538,043 A | 7/1996 | Salazar |
| 5,540,562 A | 7/1996 | Giter |
| 5,544,519 A | 8/1996 | Hammarberg et al. |
| 5,545,252 A | 8/1996 | Hinshaw et al. |
| 5,551,391 A | 9/1996 | Beck et al. |
| 5,554,177 A | 9/1996 | Kieval et al. |
| 5,556,421 A | 9/1996 | Prutchi et al. |
| 5,558,638 A | 9/1996 | Evers et al. |
| 5,562,079 A | 10/1996 | Gray, Jr. |
| 5,563,347 A | 10/1996 | Martin et al. |
| 5,566,865 A | 10/1996 | Jouillat et al. |
| 5,567,287 A | 10/1996 | Joshi et al. |
| 5,568,038 A | 10/1996 | Tatsumi |
| 5,568,884 A | 10/1996 | Bruna |
| 5,575,310 A | 11/1996 | Kamen et al. |
| 5,575,632 A | 11/1996 | Morris et al. |
| 5,575,770 A | 11/1996 | Melsky et al. |
| 5,578,005 A | 11/1996 | Sancoff et al. |
| 5,578,832 A | 11/1996 | Trulson et al. |
| 5,582,168 A | 12/1996 | Samuels et al. |
| 5,590,648 A | 1/1997 | Mitchell et al. |
| 5,593,552 A | 1/1997 | Joshi et al. |
| 5,602,040 A | 2/1997 | May et al. |
| 5,603,729 A | 2/1997 | Brown et al. |
| 5,605,701 A | 2/1997 | Bymaster et al. |
| 5,607,418 A | 3/1997 | Arzbaecher |
| 5,615,671 A | 4/1997 | Schoonen et al. |
| 5,616,123 A | 4/1997 | Cheikh |
| 5,616,132 A | 4/1997 | Newman |
| 5,617,650 A | 4/1997 | Grim |
| RE35,501 E | 5/1997 | Ross et al. |
| 5,628,349 A | 5/1997 | Diggins et al. |
| 5,628,624 A | 5/1997 | Nelson, II |
| 5,634,491 A | 6/1997 | Benedict |
| 5,634,779 A | 6/1997 | Eysymontt |
| 5,637,092 A | 6/1997 | Shaw |
| 5,637,095 A | 6/1997 | Nason et al. |
| 5,639,220 A | 6/1997 | Hawakawa |
| 5,639,441 A | 6/1997 | Sievers et al. |
| 5,639,473 A | 6/1997 | Grinstaff et al. |
| 5,641,405 A | 6/1997 | Keshaviah et al. |
| 5,643,773 A | 7/1997 | Aebisher et al. |
| 5,645,526 A | 7/1997 | Flower |
| 5,651,980 A | 7/1997 | Lanza et al. |
| 5,656,032 A | 8/1997 | Kriesel et al. |
| 5,656,501 A | 8/1997 | Yedgar et al. |
| 5,656,503 A | 8/1997 | May et al. |
| 5,658,250 A | 8/1997 | Blomquist |
| 5,659,126 A | 8/1997 | Farber |
| 5,660,150 A | 8/1997 | Anderson et al. |
| 5,665,065 A | 9/1997 | Colman et al. |
| 5,665,070 A | 9/1997 | McPhee |
| 5,669,877 A | 9/1997 | Blomquist |
| 5,671,874 A | 9/1997 | Behar et al. |
| 5,676,651 A | 10/1997 | Larson, Jr. et al. |
| 5,681,435 A | 10/1997 | Joshi et al. |
| 5,688,113 A | 11/1997 | Bareiss et al. |
| 5,688,225 A | 11/1997 | Walker |
| 5,688,232 A | 11/1997 | Flower |
| 5,693,018 A | 12/1997 | Kriesel et al. |
| 5,694,961 A | 12/1997 | Begemann et al. |
| 5,695,464 A | 12/1997 | Viallet |
| 5,702,384 A | 12/1997 | Umeyama et al. |
| 5,704,520 A | 1/1998 | Gross |
| 5,707,212 A | 1/1998 | Matthews |
| 5,707,361 A | 1/1998 | Slettenmark |
| 5,711,989 A | 1/1998 | Ciardella et al. |
| 5,712,795 A | 1/1998 | Layman et al. |
| 5,713,856 A | 2/1998 | Eggers et al. |
| 5,713,858 A | 2/1998 | Heruth et al. |
| 5,718,562 A | 2/1998 | Lawless et al. |
| 5,719,761 A | 2/1998 | Gatti et al. |
| 5,720,241 A | 2/1998 | Gail |
| 5,720,921 A | 2/1998 | Mesrol |
| 5,722,367 A | 3/1998 | Izadorek |
| 5,728,396 A | 3/1998 | Peery et al. |
| 5,730,149 A | 3/1998 | Nakayama et al. |

| Patent No. | Date | Inventor |
|---|---|---|
| 5,730,723 A | 3/1998 | Castellano et al. |
| 5,735,818 A | 4/1998 | Kriesel et al. |
| 5,738,650 A | 4/1998 | Gregg |
| 5,740,718 A | 4/1998 | Rathweg |
| 5,741,211 A | 4/1998 | Renirie et al. |
| 5,741,242 A | 4/1998 | Kriesel et al. |
| 5,743,291 A | 4/1998 | Nehm et al. |
| 5,755,683 A | 5/1998 | Houle et al. |
| 5,759,018 A | 6/1998 | Thanscheidt |
| 5,763,267 A | 6/1998 | Kurjan et al. |
| 5,763,398 A | 6/1998 | Bengtsson |
| 5,765,464 A | 6/1998 | Morita |
| 5,765,729 A | 6/1998 | Miller et al. |
| 5,769,615 A | 6/1998 | Giter |
| 5,770,149 A | 6/1998 | Raible |
| 5,770,160 A | 6/1998 | Smith et al. |
| 5,771,770 A | 6/1998 | Muller |
| 5,782,931 A | 7/1998 | Yang et al. |
| 5,785,688 A | 7/1998 | Joshi et al. |
| 5,788,671 A | 8/1998 | Johnson |
| 5,788,682 A | 8/1998 | Maget |
| 5,792,603 A | 8/1998 | Dunkelman et al. |
| 5,794,505 A | 8/1998 | Fischer et al. |
| 5,794,515 A | 8/1998 | Bethke |
| 5,797,867 A | 8/1998 | Guerrera et al. |
| 5,800,387 A | 9/1998 | Duffy et al. |
| 5,800,420 A | 9/1998 | Gross et al. |
| 5,803,319 A | 9/1998 | Smith et al. |
| 5,803,917 A | 9/1998 | Butterfield et al. |
| 5,807,315 A | 9/1998 | Van Antwerp et al. |
| 5,807,375 A | 9/1998 | Gross et al. |
| 5,810,737 A | 9/1998 | Dardik |
| 5,810,771 A | 9/1998 | Blomquist |
| 5,814,020 A | 9/1998 | Gross |
| 5,814,100 A | 9/1998 | Carpentier et al. |
| 5,820,587 A | 10/1998 | Place |
| 5,820,589 A | 10/1998 | Torgerson et al. |
| 5,820,622 A | 10/1998 | Gross et al. |
| 5,823,388 A | 10/1998 | Green |
| 5,823,746 A | 10/1998 | Johnson |
| 5,826,621 A | 10/1998 | Jemmott |
| 5,830,175 A | 11/1998 | Flower |
| 5,837,220 A | 11/1998 | Blake et al. |
| 5,837,444 A | 11/1998 | Shah |
| 5,840,071 A | 11/1998 | Kriesel et al. |
| 5,840,770 A | 11/1998 | Hill |
| 5,848,880 A | 12/1998 | Helmig |
| 5,848,990 A | 12/1998 | Cirelli et al. |
| 5,848,991 A | 12/1998 | Gross et al. |
| 5,849,031 A | 12/1998 | Martinez et al. |
| 5,849,737 A | 12/1998 | Chaplan et al. |
| 5,851,198 A | 12/1998 | Castellano et al. |
| 5,851,549 A | 12/1998 | Svec |
| 5,851,985 A | 12/1998 | Tepic et al. |
| 5,854,074 A | 12/1998 | Charlton et al. |
| 5,858,001 A | 1/1999 | Tsals et al. |
| 5,858,201 A | 1/1999 | Otsuka et al. |
| 5,858,388 A | 1/1999 | Grossman et al. |
| 5,858,393 A | 1/1999 | Bymaster et al. |
| 5,859,365 A | 1/1999 | Kataoka et al. |
| 5,860,957 A | 1/1999 | Jacobsen et al. |
| 5,863,187 A | 1/1999 | Bensley et al. |
| 5,865,603 A | 2/1999 | Francart, Jr. |
| 5,871,125 A | 2/1999 | Gross |
| 5,871,515 A | 2/1999 | Wiklund et al. |
| 5,873,857 A | 2/1999 | Kriesel |
| 5,876,189 A | 3/1999 | Lukas et al. |
| 5,876,368 A | 3/1999 | Flower |
| 5,876,370 A | 3/1999 | Blomquist |
| 5,877,146 A | 3/1999 | McKenzie et al. |
| 5,877,216 A | 3/1999 | Place et al. |
| 5,878,992 A | 3/1999 | Edwards et al. |
| 5,880,101 A | 3/1999 | Stankov |
| 5,882,494 A | 3/1999 | Van Antwerp et al. |
| 5,883,138 A | 3/1999 | Hershkowitz et al. |
| 5,885,211 A | 3/1999 | Eppstein et al. |
| 5,885,250 A | 3/1999 | Kriesel et al. |
| 5,885,614 A | 3/1999 | Hirsch |
| 5,886,056 A | 3/1999 | Hershkowitz et al. |
| 5,887,793 A | 3/1999 | Kieffer |
| 5,890,413 A | 4/1999 | Bayer et al. |
| 5,891,097 A | 4/1999 | Saito et al. |
| 5,893,708 A | 4/1999 | Nelson, II |
| 5,894,992 A | 4/1999 | Liu et al. |
| 5,895,369 A | 4/1999 | Flower |
| 5,897,530 A | 4/1999 | Jackson |
| 5,902,336 A | 5/1999 | Mishkin |
| 5,903,710 A | 5/1999 | Wefler et al. |
| 5,912,005 A | 6/1999 | Lanza et al. |
| 5,916,191 A | 6/1999 | Plunkett et al. |
| 5,919,156 A | 7/1999 | Stropkay et al. |
| 5,919,209 A | 7/1999 | Schouten |
| 5,919,216 A | 7/1999 | Houben et al. |
| 5,924,456 A | 7/1999 | Simon |
| 5,925,629 A | 7/1999 | Place |
| 5,928,194 A | 7/1999 | Maget |
| 5,928,281 A | 7/1999 | Huynh et al. |
| 5,931,814 A | 8/1999 | Alex et al. |
| 5,933,287 A | 8/1999 | Muller |
| 5,935,099 A | 8/1999 | Peeterson et al. |
| 5,935,168 A | 8/1999 | Yang et al. |
| 5,935,598 A | 8/1999 | Sage et al. |
| 5,938,636 A | 8/1999 | Kramer et al. |
| 5,938,640 A | 8/1999 | Maget |
| 5,941,846 A | 8/1999 | Duffy et al. |
| 5,948,367 A * | 9/1999 | Gmeiner et al. ............ 422/111 |
| 5,950,879 A | 9/1999 | Ritsche |
| 5,951,523 A | 9/1999 | Osterlund et al. |
| 5,954,697 A | 9/1999 | Srisathapat et al. |
| 5,954,752 A | 9/1999 | Mongeon et al. |
| 5,957,861 A | 9/1999 | Combs et al. |
| 5,957,885 A | 9/1999 | Bollish et al. |
| 5,957,889 A | 9/1999 | Poulson et al. |
| 5,957,895 A | 9/1999 | Sage et al. |
| 5,958,760 A | 9/1999 | Freeman |
| 5,961,483 A | 10/1999 | Sage et al. |
| 5,962,566 A | 10/1999 | Grandfills et al. |
| 5,964,724 A | 10/1999 | Rivera et al. |
| 5,973,012 A | 10/1999 | Behrmann et al. |
| 5,980,596 A | 11/1999 | Hershkowitz et al. |
| 5,983,976 A | 11/1999 | Kono |
| 5,984,894 A | 11/1999 | Poulson et al. |
| 5,984,897 A | 11/1999 | Peterson et al. |
| 5,984,906 A | 11/1999 | Bonnichsen et al. |
| 5,985,305 A | 11/1999 | Peery et al. |
| 5,988,165 A | 11/1999 | Richey et al. |
| 5,988,998 A | 11/1999 | Glover |
| 5,989,238 A | 11/1999 | Ginsburg |
| 5,992,695 A | 11/1999 | Start |
| 5,997,501 A | 12/1999 | Gross et al. |
| 5,997,518 A | 12/1999 | Laibovitz et al. |
| 6,001,585 A | 12/1999 | Gramer |
| 6,003,736 A | 12/1999 | Ljunggren |
| 6,006,800 A | 12/1999 | Nakano |
| 6,007,314 A | 12/1999 | Nelson, II |
| 6,012,492 A | 1/2000 | Kozyuk |
| 6,013,020 A | 1/2000 | Meloul et al. |
| 6,016,044 A | 1/2000 | Holdaway |
| 6,017,318 A | 1/2000 | Gauthier |
| 6,017,545 A | 1/2000 | Modi |
| 6,023,641 A | 2/2000 | Thompson |
| 6,024,009 A | 2/2000 | Morita |
| 6,024,539 A | 2/2000 | Blomquist |
| 6,030,358 A | 2/2000 | Odland |
| 6,033,377 A | 3/2000 | Rasmussen et al. |
| 6,034,054 A | 3/2000 | DeFelippis et al. |
| 6,035,639 A | 3/2000 | Kolmanovsky et al. |
| 6,037,346 A | 3/2000 | Doherty, Jr. et al. |
| 6,038,960 A | 3/2000 | Fukushima et al. |
| 6,042,561 A | 3/2000 | Ash et al. |
| 6,048,337 A | 4/2000 | Svedman |
| 6,051,256 A | 4/2000 | Platz et al. |
| 6,056,522 A | 5/2000 | Johnson |
| 6,059,507 A | 5/2000 | Adams |
| 6,059,753 A | 5/2000 | Faust et al. |
| 6,062,022 A | 5/2000 | Folsom et al. |
| 6,062,531 A | 5/2000 | Rapp et al. |
| 6,063,053 A | 5/2000 | Castellano et al. |

| | | | |
|---|---|---|---|
| 6,065,279 A | 5/2000 | Kuromitsu et al. | |
| 6,065,289 A | 5/2000 | Phillips | |
| 6,065,941 A | 5/2000 | Gray et al. | |
| 6,071,423 A | 6/2000 | Brown et al. | |
| 6,073,048 A | 6/2000 | Kieval et al. | |
| 6,074,359 A | 6/2000 | Keshaviah et al. | |
| 6,077,246 A | 6/2000 | Kullas et al. | |
| 6,080,130 A | 6/2000 | Castellano et al. | |
| 6,083,602 A | 7/2000 | Caldwell et al. | |
| 6,083,710 A | 7/2000 | Heller et al. | |
| 6,086,562 A | 7/2000 | Jacobson et al. | |
| 6,093,167 A | 7/2000 | Houben et al. | |
| 6,093,312 A | 7/2000 | Boulter | |
| 6,095,134 A | 8/2000 | Sievers et al. | |
| 6,096,216 A | 8/2000 | Shanbrom et al. | |
| 6,099,293 A | 8/2000 | Kern et al. | |
| 6,099,495 A | 8/2000 | Kinghorn et al. | |
| 6,099,504 A | 8/2000 | Gross et al. | |
| 6,102,127 A | 8/2000 | Pierce | |
| 6,103,033 A | 8/2000 | Say et al. | |
| 6,103,275 A | 8/2000 | Seitz et al. | |
| 6,106,477 A | 8/2000 | Miesel et al. | |
| 6,109,896 A | 8/2000 | Schuller et al. | |
| 6,110,148 A | 8/2000 | Brown et al. | |
| 6,110,152 A | 8/2000 | Kovelman | |
| 6,110,427 A | 8/2000 | Uffenheimer | |
| RE36,871 E | 9/2000 | Epstein et al. | |
| 6,113,782 A | 9/2000 | Leonard | |
| 6,120,460 A | 9/2000 | Abreu | |
| 6,122,536 A | 9/2000 | Sun et al. | |
| 6,123,175 A | 9/2000 | Fett | |
| 6,123,686 A | 9/2000 | Olsen et al. | |
| 6,126,956 A | 10/2000 | Grossman et al. | |
| 6,127,363 A | 10/2000 | Doherty, Jr. et al. | |
| 6,132,686 A | 10/2000 | Gallup et al. | |
| 6,135,196 A | 10/2000 | Kono | |
| 6,135,978 A | 10/2000 | Houben et al. | |
| 6,142,939 A | 11/2000 | Eppstein et al. | |
| 6,143,238 A | 11/2000 | Konishi et al. | |
| 6,143,252 A | 11/2000 | Haxo, Jr. et al. | |
| 6,144,866 A | 11/2000 | Miesel et al. | |
| 6,145,625 A | 11/2000 | Prokop et al. | |
| 6,147,070 A | 11/2000 | Facchini | |
| 6,147,109 A | 11/2000 | Liao et al. | |
| 6,152,898 A | 11/2000 | Olsen | |
| 6,155,748 A | 12/2000 | Allen et al. | |
| 6,156,753 A | 12/2000 | Doherty, Jr. et al. | |
| 6,158,431 A | 12/2000 | Poole | |
| 6,158,965 A | 12/2000 | Butterfield et al. | |
| 6,163,721 A | 12/2000 | Thompson | |
| 6,164,924 A | 12/2000 | Gruett et al. | |
| 6,165,155 A | 12/2000 | Jacobson et al. | |
| 6,167,290 A | 12/2000 | Yang et al. | |
| 6,168,575 B1 | 1/2001 | Soultanpour | |
| 6,175,752 B1 | 1/2001 | Say et al. | |
| 6,176,692 B1 | 1/2001 | Reinartz et al. | |
| 6,178,996 B1 | 1/2001 | Suzuki | |
| 6,179,583 B1 | 1/2001 | Weston | |
| 6,180,597 B1 | 1/2001 | Liao et al. | |
| 6,185,460 B1 | 2/2001 | Thompson | |
| 6,186,982 B1 | 2/2001 | Gross et al. | |
| 6,198,383 B1 | 3/2001 | Sekura et al. | |
| 6,205,961 B1 | 3/2001 | Bailey et al. | |
| 6,210,135 B1 | 4/2001 | Rassin et al. | |
| 6,210,361 B1 | 4/2001 | Kamen et al. | |
| 6,210,957 B1 | 4/2001 | Carpentier et al. | |
| 6,211,147 B1 | 4/2001 | Unemori | |
| 6,211,426 B1 | 4/2001 | Abrams | |
| 6,212,948 B1 | 4/2001 | Ekdahl et al. | |
| 6,217,826 B1 | 4/2001 | Reeder et al. | |
| 6,218,666 B1 | 4/2001 | Lukica et al. | |
| 6,221,378 B1 | 4/2001 | Modi | |
| 6,223,080 B1 | 5/2001 | Thompson | |
| 6,223,703 B1 | 5/2001 | Galvin | |
| 6,223,746 B1 * | 5/2001 | Jewett et al. .............. 128/203.12 |
| 6,224,347 B1 | 5/2001 | Clark et al. | |
| 6,224,352 B1 | 5/2001 | Hauser et al. | |
| 6,227,818 B1 | 5/2001 | Falk et al. | |
| 6,228,044 B1 | 5/2001 | Jensen et al. | |
| 6,229,584 B1 | 5/2001 | Chuo et al. | |
| 6,231,882 B1 | 5/2001 | Modi | |
| 6,236,887 B1 | 5/2001 | Ben-Hamin et al. | |
| 6,238,423 B1 | 5/2001 | Bardy | |
| 6,241,704 B1 | 6/2001 | Peterson et al. | |
| 6,241,743 B1 | 6/2001 | Levin et al. | |
| 6,245,347 B1 | 6/2001 | Zhang et al. | |
| 6,247,493 B1 | 6/2001 | Henderson | |
| 6,248,067 B1 | 6/2001 | Causey, III et al. | |
| 6,248,093 B1 | 6/2001 | Moberg | |
| 6,248,280 B1 | 6/2001 | Kern et al. | |
| 6,251,932 B1 | 6/2001 | Reicht et al. | |
| 6,254,355 B1 | 7/2001 | Gharib | |
| 6,256,533 B1 | 7/2001 | Yuzhakov et al. | |
| 6,257,178 B1 | 7/2001 | Laimbock | |
| 6,257,191 B1 | 7/2001 | Kutlucinar | |
| 6,261,272 B1 | 7/2001 | Gross et al. | |
| 6,261,280 B1 | 7/2001 | Houbin et al. | |
| 6,264,439 B1 | 7/2001 | Falk et al. | |
| 6,264,680 B1 | 7/2001 | Ash et al. | |
| 6,266,564 B1 | 7/2001 | Hill et al. | |
| 6,270,478 B1 | 8/2001 | Mernoe | |
| 6,275,717 B1 | 8/2001 | Gross et al. | |
| 6,276,434 B1 | 8/2001 | Kono | |
| 6,277,819 B1 | 8/2001 | Efendic | |
| 6,280,408 B1 | 8/2001 | Sipin | |
| 6,280,416 B1 | 8/2001 | Van Antwerp et al. | |
| 6,283,197 B1 | 9/2001 | Kono | |
| 6,283,944 B1 | 9/2001 | McMullen et al. | |
| 6,283,949 B1 | 9/2001 | Roorda | |
| 6,284,725 B1 | 9/2001 | Coolidge et al. | |
| 6,288,518 B1 | 9/2001 | Yang et al. | |
| 6,293,242 B1 | 9/2001 | Kutlucinar | |
| 6,293,429 B2 * | 9/2001 | Sadler et al. .................. 222/61 |
| 6,294,550 B1 | 9/2001 | Place et al. | |
| 6,296,456 B1 | 10/2001 | Thornelow et al. | |
| 6,298,760 B1 | 10/2001 | Truttmann et al. | |
| 6,298,941 B1 | 10/2001 | Spadafora | |
| 6,299,415 B1 | 10/2001 | Bahrton | |
| 6,302,107 B1 | 10/2001 | Richey et al. | |
| 6,302,653 B1 | 10/2001 | Bryant et al. | |
| 6,302,855 B1 | 10/2001 | Lav et al. | |
| 6,306,420 B1 | 10/2001 | Cheikh | |
| 6,306,841 B1 | 10/2001 | Place et al. | |
| 6,310,270 B1 | 10/2001 | Huang et al. | |
| 6,312,409 B1 | 11/2001 | Gross | |
| 6,314,317 B1 | 11/2001 | Willis | |
| 6,315,769 B1 | 11/2001 | Peer et al. | |
| 6,319,215 B1 | 11/2001 | Manor et al. | |
| 6,319,245 B1 | 11/2001 | Berrigan | |
| 6,323,022 B1 | 11/2001 | Chang et al. | |
| 6,325,999 B1 | 12/2001 | Bellgrau et al. | |
| 6,327,964 B1 | 12/2001 | Schuller et al. | |
| 6,328,004 B1 | 12/2001 | Rynhart | |
| 6,331,172 B1 | 12/2001 | Epstein et al. | |
| 6,334,761 B1 | 1/2002 | Tai et al. | |
| 6,338,942 B2 | 1/2002 | Kraus et al. | |
| 6,340,783 B1 | 1/2002 | Snow | |
| 6,342,037 B1 | 1/2002 | Roe et al. | |
| 6,342,484 B1 | 1/2002 | Kulkarni et al. | |
| 6,344,457 B1 | 2/2002 | Jeanpetit et al. | |
| 6,346,095 B1 | 2/2002 | Gross et al. | |
| 6,350,589 B1 | 2/2002 | Morris et al. | |
| 6,355,030 B1 | 3/2002 | Aldrich et al. | |
| 6,358,519 B1 | 3/2002 | Waterman | |
| 6,364,865 B1 | 4/2002 | Lavi et al. | |
| 6,365,185 B1 | 4/2002 | Ritchel et al. | |
| 6,365,628 B1 | 4/2002 | Berge | |
| 6,366,808 B1 | 4/2002 | Schroeppel et al. | |
| 6,368,272 B1 | 4/2002 | Porumbescu | |
| 6,371,732 B1 | 4/2002 | Moubayed et al. | |
| 6,372,182 B1 | 4/2002 | Mauro et al. | |
| 6,372,508 B1 | 4/2002 | Shnizer et al. | |
| 6,374,683 B1 | 4/2002 | Hunicke-Smith et al. | |
| 6,381,493 B1 | 4/2002 | Stadler et al. | |
| 6,382,923 B1 | 5/2002 | gray | |
| 6,393,893 B1 | 5/2002 | Fetz et al. | |
| 6,395,292 B2 | 5/2002 | Peery et al. | |
| 6,395,536 B2 | 5/2002 | Freeman | |

| Patent | Date | Inventor |
|---|---|---|
| 6,397,199 B1 | 5/2002 | Goodwin, III |
| 6,398,718 B1 | 6/2002 | Yachia et al. |
| 6,398,760 B1 | 6/2002 | Danby |
| 6,399,024 B1 | 6/2002 | Bevirt et al. |
| 6,402,689 B1 | 6/2002 | Scarantino et al. |
| 6,406,455 B1 | 6/2002 | Willis et al. |
| 6,409,698 B1 | 6/2002 | Robinson et al. |
| 6,412,273 B1 | 7/2002 | Rohs |
| 6,413,238 B1 | 7/2002 | Maget et al. |
| 6,413,254 B1 | 7/2002 | Hissong et al. |
| 6,415,961 B2 | 7/2002 | Bonnigue |
| 6,416,215 B1 | 7/2002 | Terentiev |
| 6,416,291 B1 | 7/2002 | Butterfield et al. |
| 6,416,293 B1 * | 7/2002 | Bouchard et al. ............... 417/53 |
| 6,420,169 B1 | 7/2002 | Read et al. |
| 6,422,256 B1 | 7/2002 | Balazy et al. |
| 6,423,029 B1 | 7/2002 | Elsberry |
| 6,423,035 B1 | 7/2002 | Das et al. |
| 6,423,344 B1 | 7/2002 | Platz et al. |
| 6,425,740 B1 | 7/2002 | Jacobsen et al. |
| 6,427,088 B1 | 7/2002 | Bowman, IV et al. |
| 6,428,491 B1 | 8/2002 | Weiss |
| 6,429,197 B1 | 8/2002 | Coolidge et al. |
| 6,429,230 B1 | 8/2002 | Cavazza |
| 6,429,232 B1 | 8/2002 | Kinsella et al. |
| 6,433,040 B1 | 8/2002 | Dellamary et al. |
| 6,436,072 B1 | 8/2002 | Kullas et al. |
| 6,436,078 B1 | 8/2002 | Svedman |
| 6,438,408 B1 | 8/2002 | Mulligan et al. |
| 6,440,096 B1 | 8/2002 | Lastovich et al. |
| 6,441,036 B1 | 8/2002 | Berge |
| 6,443,097 B1 | 9/2002 | Zohar et al. |
| 6,443,942 B2 | 9/2002 | Van Antwerp |
| 6,446,513 B1 | 9/2002 | Henderson |
| 6,447,443 B1 | 9/2002 | Keogh et al. |
| 6,447,446 B1 | 9/2002 | Smith et al. |
| 6,447,475 B1 | 9/2002 | Castellano et al. |
| 6,447,522 B2 | 9/2002 | Gambale et al. |
| 6,450,942 B1 | 9/2002 | Lapanashvili et al. |
| 6,454,707 B1 | 9/2002 | Casscells, III |
| 6,454,785 B2 | 9/2002 | De Hoyos Garza |
| 6,457,956 B1 | 10/2002 | Hauser et al. |
| 6,458,102 B1 | 10/2002 | Mann et al. |
| 6,458,109 B1 | 10/2002 | Henley et al. |
| 6,458,256 B1 | 10/2002 | Zhong |
| 6,458,762 B1 | 10/2002 | McKenzie et al. |
| 6,461,329 B1 | 10/2002 | Van Antwerp et al. |
| 6,461,331 B1 | 10/2002 | Van Antwerp |
| 6,461,334 B1 | 10/2002 | Buch-Rasmussen et al. |
| 6,461,828 B1 | 10/2002 | Stanton et al. |
| 6,463,794 B1 | 10/2002 | Moshe et al. |
| 6,464,667 B1 | 10/2002 | Kamen et al. |
| 6,467,267 B2 | 10/2002 | Kanazawa et al. |
| 6,468,200 B1 | 10/2002 | Fischi |
| 6,469,016 B1 | 10/2002 | Place et al. |
| 6,471,496 B1 | 10/2002 | Merklein et al. |
| 6,471,689 B1 | 10/2002 | Joseph et al. |
| 6,471,855 B1 | 10/2002 | Odak et al. |
| 6,472,434 B1 | 10/2002 | Place et al. |
| 6,474,219 B2 | 11/2002 | Klitmose et al. |
| 6,475,180 B2 | 11/2002 | Peterson et al. |
| 6,475,750 B1 | 11/2002 | Han et al. |
| 6,477,774 B1 | 11/2002 | Marando et al. |
| 6,478,385 B1 | 11/2002 | Nishii et al. |
| 6,478,771 B1 | 11/2002 | Lavi et al. |
| 6,482,186 B1 | 11/2002 | Douglas et al. |
| 6,484,906 B2 | 11/2002 | Bonnigue |
| 6,485,263 B1 | 11/2002 | Bryant et al. |
| 6,485,452 B1 | 11/2002 | French et al. |
| 6,485,461 B1 | 11/2002 | Mason et al. |
| 6,488,652 B1 | 12/2002 | Weijand et al. |
| 6,488,697 B1 | 12/2002 | Ariura et al. |
| 6,489,346 B1 | 12/2002 | Phillips |
| 6,490,483 B2 | 12/2002 | Willis |
| 6,494,865 B1 | 12/2002 | Alchas |
| 6,500,150 B1 | 12/2002 | Gross et al. |
| 6,505,059 B1 | 1/2003 | Kollias et al. |
| 6,506,594 B1 | 1/2003 | Barany et al. |
| 6,508,788 B2 | 1/2003 | Preuthun |
| 6,511,435 B1 | 1/2003 | Bluth et al. |
| 6,512,949 B1 | 1/2003 | Combs et al. |
| 6,514,689 B2 | 2/2003 | Han et al. |
| 6,517,482 B1 | 2/2003 | Elden et al. |
| 6,522,980 B1 | 2/2003 | Arnold |
| 6,530,900 B1 | 3/2003 | Daily et al. |
| 6,533,183 B2 | 3/2003 | Aasmul et al. |
| 6,537,241 B1 | 3/2003 | Odland |
| 6,537,251 B2 | 3/2003 | Kiltmose |
| 6,537,272 B2 | 3/2003 | Christopherson et al. |
| 6,540,006 B2 | 4/2003 | Kono |
| 6,540,161 B1 | 4/2003 | Gordon |
| 6,540,727 B2 | 4/2003 | Harper et al. |
| 6,540,996 B1 | 4/2003 | Zwaal et al. |
| 6,541,021 B1 | 4/2003 | Johnson et al. |
| 6,542,774 B2 | 4/2003 | Hill et al. |
| 6,542,775 B2 | 4/2003 | Ding et al. |
| 6,544,212 B2 | 4/2003 | Galley et al. |
| 6,550,245 B2 | 4/2003 | Nishii et al. |
| 6,551,276 B1 | 4/2003 | Mann et al. |
| 6,551,992 B1 | 4/2003 | DeFelippis et al. |
| 6,553,245 B1 | 4/2003 | Grace et al. |
| 6,554,798 B1 | 4/2003 | Mann et al. |
| 6,557,454 B2 | 5/2003 | Miyazawa |
| 6,558,320 B1 | 5/2003 | Causey et al. |
| 6,558,345 B1 | 5/2003 | Houben et al. |
| 6,558,351 B1 | 5/2003 | Steil et al. |
| 6,558,665 B1 | 5/2003 | Cohen et al. |
| 6,558,902 B1 | 5/2003 | Hillenkamp |
| 6,560,478 B1 | 5/2003 | Alfano et al. |
| 6,562,001 B2 | 5/2003 | Lebel et al. |
| 6,564,093 B1 | 5/2003 | Ostrow et al. |
| 6,564,104 B2 | 5/2003 | Nelson et al. |
| 6,564,105 B2 | 5/2003 | Starkweather et al. |
| 6,565,802 B1 | 5/2003 | Hanley et al. |
| 6,565,872 B2 | 5/2003 | Wu et al. |
| 6,568,898 B2 | 5/2003 | Nishimura et al. |
| 6,568,922 B1 | 5/2003 | Winsel |
| 6,569,123 B2 | 5/2003 | Alchas et al. |
| 6,569,143 B2 | 5/2003 | Alchas et al. |
| 6,569,456 B2 | 5/2003 | Faour et al. |
| 6,571,128 B2 | 5/2003 | Lebel et al. |
| 6,571,831 B1 | 6/2003 | Hart |
| 6,572,542 B1 | 6/2003 | Houben et al. |
| 6,572,566 B2 | 6/2003 | Effenhauser |
| 6,577,899 B2 | 6/2003 | Lebel et al. |
| 6,579,496 B1 | 6/2003 | Fausset et al. |
| 6,582,366 B1 | 6/2003 | Porumbescu |
| 6,582,393 B2 | 6/2003 | Sage, Jr. |
| 6,582,418 B1 | 6/2003 | Verbeek et al. |
| 6,583,111 B1 | 6/2003 | DiMarchi et al. |
| 6,585,644 B2 | 7/2003 | Lebel et al. |
| 6,585,707 B2 | 7/2003 | Cabiri et al. |
| 6,589,158 B2 | 7/2003 | Winkler |
| 6,589,229 B1 | 7/2003 | Connelly et al. |
| 6,592,544 B1 | 7/2003 | Mooney et al. |
| 6,592,571 B1 | 7/2003 | Verbeek et al. |
| 6,592,860 B1 | 7/2003 | Levy et al. |
| 6,592,904 B2 | 7/2003 | Platz et al. |
| 6,593,313 B2 | 7/2003 | Place et al. |
| 6,595,756 B2 | 7/2003 | Gray et al. |
| 6,595,948 B2 | 7/2003 | Suzuki et al. |
| 6,595,956 B1 | 7/2003 | Gross et al. |
| 6,599,281 B1 | 7/2003 | Struys et al. |
| 6,602,241 B2 | 8/2003 | Makower et al. |
| 6,604,908 B1 * | 8/2003 | Bryant et al. .................. 417/26 |
| 6,605,072 B2 | 8/2003 | Struys et al. |
| 6,607,513 B1 | 8/2003 | Down et al. |
| 6,607,658 B1 | 8/2003 | Heller et al. |
| 6,607,739 B1 | 8/2003 | Wallo |
| 6,610,003 B1 | 8/2003 | Meloul et al. |
| 6,612,535 B1 | 9/2003 | Tai et al. |
| 6,613,019 B2 | 9/2003 | Munk |
| 6,616,196 B1 | 9/2003 | Weh et al. |
| 6,616,627 B2 | 9/2003 | Willis et al. |
| 6,618,603 B2 | 9/2003 | Varalli et al. |
| 6,620,140 B1 | 9/2003 | Metzger |
| 6,620,379 B1 | 9/2003 | Piuk et al. |
| 6,623,698 B2 | 9/2003 | Kuo |

| | | |
|---|---|---|
| 6,626,644 B2 | 9/2003 | Ozaki |
| 6,629,934 B2 | 10/2003 | Mault et al. |
| 6,629,938 B1 | 10/2003 | Engvall et al. |
| 6,629,949 B1 | 10/2003 | Douglas |
| 6,634,939 B2 | 10/2003 | Johnson |
| 6,635,014 B2 | 10/2003 | Starkweather et al. |
| 6,636,796 B2 | 10/2003 | Kolmanovsky et al. |
| 6,639,381 B2 | 10/2003 | Tamura et al. |
| 6,641,533 B2 | 11/2003 | Causey et al. |
| 6,641,562 B1 | 11/2003 | Peterson et al. |
| 6,641,565 B1 | 11/2003 | Lavi et al. |
| 6,641,566 B2 | 11/2003 | Douglas et al. |
| 6,642,019 B1 | 11/2003 | Anderson et al. |
| 6,645,181 B1 | 11/2003 | Lavi et al. |
| 6,648,821 B2 | 11/2003 | Lebel et al. |
| 6,648,859 B2 | 11/2003 | Bitdinger et al. |
| 6,648,861 B2 | 11/2003 | Platt et al. |
| 6,649,403 B1 | 11/2003 | McDevitt et al. |
| 6,650,919 B2 | 11/2003 | Edelberg et al. |
| 6,651,546 B2 | 11/2003 | Sandlin |
| 6,656,148 B2 | 12/2003 | Das et al. |
| 6,656,158 B2 | 12/2003 | Mahoney et al. |
| 6,656,159 B2 | 12/2003 | Flaherty et al. |
| 6,663,359 B2 | 12/2003 | Gray |
| 6,666,821 B2 | 12/2003 | Keimel |
| 6,668,701 B1 | 12/2003 | Everitt |
| 6,669,663 B1 | 12/2003 | Thompson |
| 6,669,669 B2 | 12/2003 | Flaherty et al. |
| 6,677,320 B2 | 1/2004 | Diederich et al. |
| 6,682,497 B2 | 1/2004 | Jensen et al. |
| 6,683,690 B1 | 1/2004 | Tobias |
| 6,689,100 B2 | 2/2004 | Connelly et al. |
| 6,689,108 B2 | 2/2004 | Lavi et al. |
| 6,689,118 B2 | 2/2004 | Alchas et al. |
| 6,689,373 B2 | 2/2004 | Johnson et al. |
| 6,692,456 B1 | 2/2004 | Eppstein et al. |
| 6,692,457 B2 | 2/2004 | Flaherty et al. |
| 6,694,191 B2 | 2/2004 | Starkweather et al. |
| 6,695,011 B2 | 2/2004 | Sochtig |
| 6,696,090 B1 | 2/2004 | Nilsson et al. |
| 6,696,493 B2 | 2/2004 | Cavazza |
| 6,699,218 B2 | 3/2004 | Flaherty et al. |
| 6,699,234 B2 | 3/2004 | Yeh et al. |
| 6,699,885 B2 | 3/2004 | Phillips |
| 6,702,779 B2 | 3/2004 | Connelly et al. |
| 6,702,857 B2 | 3/2004 | Brauker et al. |
| 6,705,845 B2 | 3/2004 | Kreiger et al. |
| 6,706,008 B2 | 3/2004 | Vishnoi et al. |
| 6,706,009 B2 | 3/2004 | Diermann et al. |
| 6,706,689 B2 | 3/2004 | Coolidge et al. |
| 6,710,051 B1 | 3/2004 | Trier |
| 6,711,489 B2 | 3/2004 | Haskara et al. |
| 6,712,095 B2 | 3/2004 | Williamson et al. |
| 6,715,516 B2 | 4/2004 | Ohms et al. |
| 6,716,190 B1 | 4/2004 | Glines et al. |
| 6,718,206 B2 | 4/2004 | Casavante |
| 6,719,302 B2 | 4/2004 | Andrick |
| 6,723,068 B2 | 4/2004 | Lavi et al. |
| 6,723,072 B2 | 4/2004 | Flaherty et al. |
| 6,726,920 B1 | 4/2004 | Theeuwes et al. |
| 6,732,573 B2 | 5/2004 | Shin et al. |
| 6,733,446 B2 | 5/2004 | Lebel et al. |
| 6,734,186 B1 | 5/2004 | Maw et al. |
| 6,736,796 B2 | 5/2004 | Shekalim et al. |
| 6,738,663 B2 | 5/2004 | Schroppel et al. |
| 6,738,707 B2 | 5/2004 | Kotwicki et al. |
| 6,740,059 B2 | 5/2004 | Flaherty et al. |
| 6,740,072 B2 | 5/2004 | Starkweather et al. |
| 6,740,075 B2 | 5/2004 | Lebel et al. |
| 6,743,201 B1 | 6/2004 | Donig et al. |
| 6,744,152 B2 | 6/2004 | Kroll |
| 6,745,079 B2 | 6/2004 | King |
| 6,746,438 B1 | 6/2004 | Arnissolle |
| 6,748,930 B2 | 6/2004 | Bofinger et al. |
| 6,749,403 B2 | 6/2004 | Bryant et al. |
| 6,749,587 B2 | 6/2004 | Flaherty et al. |
| 6,752,785 B2 | 6/2004 | Van Antwerp et al. |
| 6,752,787 B1 | 6/2004 | Causey, III et al. |
| 6,755,628 B1 | 6/2004 | Howell |
| 6,758,593 B1 | 7/2004 | Terentiev |
| 6,759,386 B2 | 7/2004 | Franco |
| 6,767,188 B2 | 7/2004 | Vrane et al. |
| 6,767,896 B1 | 7/2004 | McIntosh et al. |
| 6,768,425 B2 | 7/2004 | Flaherty et al. |
| 6,769,384 B2 | 8/2004 | Dougherty |
| 6,770,054 B1 | 8/2004 | Smolyarov et al. |
| 6,773,669 B1 | 8/2004 | Holaday et al. |
| 6,773,739 B2 | 8/2004 | Hauck et al. |
| 6,776,776 B2 | 8/2004 | Alchas et al. |
| 6,780,156 B2 | 8/2004 | Haueter et al. |
| 6,780,171 B2 | 8/2004 | Gabel et al. |
| 6,780,426 B2 | 8/2004 | Zhang et al. |
| 6,780,770 B2 | 8/2004 | Larson |
| 6,780,836 B2 | 8/2004 | Unemori |
| 6,783,107 B2 | 8/2004 | Chatufale |
| 6,783,328 B2 | 8/2004 | Lucke et al. |
| 6,786,246 B2 | 9/2004 | Ohms et al. |
| 6,790,670 B2 | 9/2004 | Munagavalasa et al. |
| 6,796,956 B2 | 9/2004 | Hartlaub et al. |
| 6,801,420 B2 | 10/2004 | Talbot et al. |
| 6,804,002 B2 | 10/2004 | Fine et al. |
| 6,804,555 B2 | 10/2004 | Warkentin |
| 6,805,122 B2 | 10/2004 | Richey, II et al. |
| 6,805,687 B2 | 10/2004 | Dextradeur et al. |
| 6,808,506 B2 | 10/2004 | Lastovich et al. |
| 6,810,290 B2 | 10/2004 | Lebel et al. |
| RE38,654 E | 11/2004 | Hill et al. |
| 6,811,534 B2 | 11/2004 | Bowman, IV et al. |
| 6,811,792 B2 | 11/2004 | Roser et al. |
| 6,813,519 B2 | 11/2004 | Lebel et al. |
| 6,813,964 B1 | 11/2004 | Clark et al. |
| 6,821,249 B2 | 11/2004 | Casscells, III et al. |
| 6,821,484 B1 | 11/2004 | Gregersen |
| 6,824,529 B2 | 11/2004 | Gross et al. |
| 6,827,524 B2 | 12/2004 | Starry, Jr. et al. |
| 6,827,702 B2 | 12/2004 | Lebel et al. |
| 6,827,710 B1 | 12/2004 | Mooney et al. |
| 6,827,898 B1 | 12/2004 | Fausset et al. |
| 6,828,552 B2 | 12/2004 | Hartley |
| 6,830,558 B2 | 12/2004 | Flaherty et al. |
| 6,830,560 B1 | 12/2004 | Gross et al. |
| 6,835,175 B1 | 12/2004 | Porumbescu |
| 6,835,194 B2 | 12/2004 | Johnson et al. |
| 6,842,642 B2 | 1/2005 | Vanhout |
| 6,843,782 B2 | 1/2005 | Gross et al. |
| 6,847,898 B1 | 1/2005 | Chen et al. |
| 6,851,449 B2 | 2/2005 | Kleibrink |
| 6,852,104 B2 | 2/2005 | Blomquist |
| 6,852,487 B1 | 2/2005 | Barany et al. |
| 6,854,432 B2 | 2/2005 | Hirano |
| 6,854,620 B2 | 2/2005 | Ramey |
| 6,858,011 B2 | 2/2005 | Sehgal |
| 6,858,403 B2 | 2/2005 | Han et al. |
| 6,864,101 B1 | 3/2005 | Winkler et al. |
| 6,867,196 B1 | 3/2005 | Wolff et al. |
| 6,868,358 B2 | 3/2005 | Brown, Jr. |
| 6,872,200 B2 | 3/2005 | Mann et al. |
| 6,873,268 B2 | 3/2005 | Lebel et al. |
| 6,876,885 B2 | 4/2005 | Swoyer et al. |
| 6,877,713 B1 | 4/2005 | Gray et al. |
| 6,880,564 B2 | 4/2005 | Erickson |
| 6,884,122 B2 | 4/2005 | Robinson et al. |
| 6,884,228 B2 | 4/2005 | Brown et al. |
| 6,885,881 B2 | 4/2005 | Leonhardt |
| 6,885,888 B2 | 4/2005 | Rezai |
| 6,886,556 B2 | 5/2005 | Fuchs |
| 6,892,755 B2 | 5/2005 | Black |
| 6,894,024 B2 | 5/2005 | Coolidge et al. |
| 6,896,666 B2 | 5/2005 | Kochamba |
| 6,899,699 B2 | 5/2005 | Enggaard |
| RE38,749 E | 6/2005 | Dardik |
| 6,905,479 B1 * | 6/2005 | Bouchard et al. ............. 604/151 |
| 6,906,028 B2 | 6/2005 | DeFelippis et al. |
| 6,908,591 B2 | 6/2005 | MacPhee et al. |
| 6,909,840 B2 | 6/2005 | Harwig et al. |
| 6,912,425 B2 | 6/2005 | Nova et al. |
| 6,913,933 B2 | 7/2005 | Jacobs et al. |
| 6,914,076 B2 | 7/2005 | Cavazza |

| | | | | | | |
|---|---|---|---|---|---|---|
| 6,916,159 | B2 | 7/2005 | Rush et al. | 7,015,782 B2 | 3/2006 | Kincaid et al. |
| 6,918,542 | B2 | 7/2005 | Silverbrook et al. | 7,018,360 B2 | 3/2006 | Flaherty et al. |
| 6,923,006 | B2 * | 8/2005 | Walton et al. .................. 62/3.64 | 7,018,361 B2 | 3/2006 | Gillespie, Jr. et al. |
| 6,923,180 | B2 | 8/2005 | Richey, II et al. | 7,018,630 B2 | 3/2006 | Takaoka |
| 6,923,764 | B2 | 8/2005 | Aceti et al. | 7,022,071 B2 | 4/2006 | Schaupp et al. |
| 6,926,694 | B2 | 8/2005 | Marano-Ford et al. | 7,022,072 B2 | 4/2006 | Fox et al. |
| 6,930,093 | B2 | 8/2005 | Brantl | 7,022,087 B2 | 4/2006 | Dempster et al. |
| 6,931,845 | B2 | 8/2005 | Schaeffer | 7,022,108 B2 | 4/2006 | Marano-Ford et al. |
| 6,931,925 | B2 | 8/2005 | Huemer et al. | 7,024,244 B2 | 4/2006 | Muhlenberg et al. |
| 6,932,114 | B2 | 8/2005 | Sparks | 7,024,245 B2 | 4/2006 | Lebel et al. |
| 6,932,796 | B2 | 8/2005 | Sage et al. | 7,025,716 B1 | 4/2006 | Meloul et al. |
| 6,935,531 | B1 | 8/2005 | Clayton | 7,025,743 B2 | 4/2006 | Mann et al. |
| 6,935,539 | B2 | 8/2005 | Krieger et al. | 7,027,478 B2 | 4/2006 | Ackley |
| 6,936,026 | B2 | 8/2005 | Diermann et al. | 7,029,455 B2 | 4/2006 | Flaherty |
| 6,936,029 | B2 | 8/2005 | Mann et al. | 7,033,843 B2 | 4/2006 | Hasegawa et al. |
| 6,936,046 | B2 | 8/2005 | Hissong et al. | 7,047,070 B2 | 5/2006 | Wilkinson et al. |
| 6,939,323 | B2 | 9/2005 | Angel et al. | 7,048,193 B2 | 5/2006 | Tsukada et al. |
| 6,939,324 | B2 | 9/2005 | Gonneli et al. | 7,048,951 B1 | 5/2006 | Seitz et al. |
| 6,942,636 | B2 | 9/2005 | Holst et al. | 7,052,251 B2 | 5/2006 | Nason et al. |
| 6,943,034 | B1 | 9/2005 | Winkler et al. | 7,053,761 B2 | 5/2006 | Schofield et al. |
| 6,946,117 | B1 | 9/2005 | Schutt et al. | 7,056,179 B2 | 6/2006 | Courtney |
| 6,948,918 | B2 | 9/2005 | Hansen | 7,056,302 B2 | 6/2006 | Douglas |
| 6,949,081 | B1 | 9/2005 | Chance | 7,056,494 B2 | 6/2006 | Adjei et al. |
| 6,950,708 | B2 | 9/2005 | Bowman, IV et al. | 7,056,887 B2 | 6/2006 | Coolidge et al. |
| 6,951,165 | B2 | 10/2005 | Kuhn et al. | 7,058,438 B2 | 6/2006 | Grace et al. |
| 6,951,553 | B2 | 10/2005 | Bubb et al. | 7,059,348 B2 | 6/2006 | Nat |
| 6,952,604 | B2 | 10/2005 | DeNuzzio et al. | 7,060,856 B2 | 6/2006 | Macikenas et al. |
| 6,952,963 | B2 | 10/2005 | DeInevo | 7,064,472 B2 | 6/2006 | Pelrine et al. |
| 6,955,819 | B2 | 10/2005 | Zhang et al. | 7,066,359 B2 | 6/2006 | Greiner-Perth |
| 6,955,915 | B2 | 10/2005 | Fodor et al. | 7,066,910 B2 | 6/2006 | Bauhahn et al. |
| 6,956,204 | B2 | 10/2005 | Dong et al. | 7,066,915 B2 | 6/2006 | Olsen |
| 6,957,655 | B2 | 10/2005 | Erickson et al. | 7,066,922 B2 | 6/2006 | Angel et al. |
| 6,957,924 | B1 | 10/2005 | McMeekin et al. | 7,069,075 B2 | 6/2006 | Olson |
| 6,958,073 | B2 | 10/2005 | Rogers et al. | 7,070,577 B1 | 7/2006 | Haller et al. |
| 6,958,705 | B2 | 10/2005 | Lebel et al. | 7,073,485 B2 | 7/2006 | Truscott et al. |
| 6,960,184 | B2 | 11/2005 | Willis et al. | 7,073,713 B2 | 7/2006 | Silverbrook et al. |
| 6,960,192 | B1 | 11/2005 | Flaherty et al. | 7,074,200 B1 | 7/2006 | Lewis |
| 6,962,103 | B2 | 11/2005 | Sandlin | 7,077,822 B1 | 7/2006 | Howard, III |
| 6,962,151 | B1 | 11/2005 | Knoch et al. | 7,078,163 B2 | 7/2006 | Torrianni |
| 6,963,770 | B2 | 11/2005 | Scarantino et al. | 7,081,105 B2 | 7/2006 | Reilly et al. |
| 6,966,325 | B2 | 11/2005 | Erickson | 7,082,812 B2 | 8/2006 | Lenormand et al. |
| 6,969,369 | B2 | 11/2005 | Struble | 7,083,108 B2 | 8/2006 | Silverbrook et al. |
| 6,970,741 | B1 | 11/2005 | Whitehurst et al. | 7,083,592 B2 | 8/2006 | Lastovich et al. |
| 6,970,742 | B2 | 11/2005 | Mann et al. | 7,083,599 B2 | 8/2006 | Alchas et al. |
| 6,971,999 | B2 | 12/2005 | Py et al. | 7,089,608 B2 | 8/2006 | Erb |
| 6,974,055 | B2 | 12/2005 | Moore et al. | 7,090,648 B2 | 8/2006 | Sackner et al. |
| 6,974,115 | B2 | 12/2005 | Silva | 7,091,179 B2 | 8/2006 | Franco |
| 6,974,437 | B2 | 12/2005 | Lebel et al. | 7,092,011 B2 | 8/2006 | Silverbrook et al. |
| 6,974,588 | B1 | 12/2005 | Miranda et al. | 7,095,210 B2 | 8/2006 | Tamura et al. |
| 6,979,308 | B1 | 12/2005 | MacDonald et al. | 7,096,889 B1 | 8/2006 | Roys |
| 6,979,316 | B1 | 12/2005 | Rubin et al. | 7,097,104 B2 | 8/2006 | Silverbrook et al. |
| 6,979,326 | B2 | 12/2005 | Mann et al. | 7,098,803 B2 | 8/2006 | Mann et al. |
| 6,980,855 | B2 | 12/2005 | Cho | 7,104,973 B2 | 9/2006 | Woolston et al. |
| 6,981,499 | B2 | 1/2006 | Anderson et al. | 7,104,981 B2 | 9/2006 | Elkins et al. |
| 6,981,967 | B2 | 1/2006 | Massengale et al. | 7,107,706 B1 | 9/2006 | Bailey, Sr. et al. |
| 6,982,248 | B2 | 1/2006 | Coolidge et al. | 7,108,491 B2 | 9/2006 | Ganser |
| 6,983,209 | B2 | 1/2006 | Jaynes | 7,108,679 B2 | 9/2006 | Alchas |
| 6,985,770 | B2 | 1/2006 | Nyhart, Jr. | 7,109,878 B2 | 9/2006 | Mann et al. |
| 6,985,771 | B2 | 1/2006 | Fischell et al. | 7,111,346 B2 | 9/2006 | Inman et al. |
| 6,986,867 | B2 | 1/2006 | Hanley et al. | 7,115,108 B2 | 10/2006 | Wilkinson et al. |
| 6,987,129 | B2 | 1/2006 | Mak et al. | 7,118,351 B2 | 10/2006 | Effenhauser et al. |
| 6,990,809 | B2 | 1/2006 | Abouraphael | 7,118,676 B2 | 10/2006 | Mueth et al. |
| 6,991,619 | B2 | 1/2006 | Marano-Ford et al. | 7,122,151 B2 | 10/2006 | Reeder et al. |
| 6,991,620 | B2 | 1/2006 | Marano-Ford et al. | 7,127,292 B2 | 10/2006 | Warman et al. |
| 6,993,795 | B2 | 2/2006 | Prineppi | 7,128,727 B2 | 10/2006 | Flaherty et al. |
| 6,994,700 | B2 | 2/2006 | Elkins et al. | 7,128,730 B2 | 10/2006 | Marano-Ford et al. |
| 6,997,202 | B2 | 2/2006 | Olander | 7,133,329 B2 | 11/2006 | Skyggebjerg et al. |
| 6,997,911 | B2 | 2/2006 | Klitmose | 7,136,701 B2 | 11/2006 | Greatbatch et al. |
| 6,997,920 | B2 | 2/2006 | Mann et al. | 7,137,951 B2 | 11/2006 | Pilarski |
| 6,998,387 | B1 | 2/2006 | Goke et al. | 7,137,964 B2 | 11/2006 | Flaherty |
| 6,998,404 | B2 | 2/2006 | Moskowitz | 7,138,141 B2 | 11/2006 | Platz et al. |
| 6,999,854 | B2 | 2/2006 | Roth | 7,140,332 B2 | 11/2006 | Klein et al. |
| 7,004,928 | B2 | 2/2006 | Aceti et al. | 7,141,425 B2 | 11/2006 | Dzekunov et al. |
| 7,008,399 | B2 | 3/2006 | Larsen et al. | 7,141,812 B2 | 11/2006 | Appleby et al. |
| 7,008,403 | B1 | 3/2006 | Mallett | 7,144,384 B2 | 12/2006 | Gorman et al. |
| 7,010,340 | B2 | 3/2006 | Scarantino et al. | 7,144,729 B2 | 12/2006 | Rolland et al. |
| 7,011,647 | B2 | 3/2006 | Purdy et al. | 7,147,386 B2 | 12/2006 | Zhang et al. |
| 7,011,682 | B2 | 3/2006 | Lashinski et al. | 7,147,839 B2 | 12/2006 | Sampath et al. |
| 7,013,727 | B2 | 3/2006 | Delnevo | 7,150,409 B2 | 12/2006 | Gonneli et al. |

| | | | | | | |
|---|---|---|---|---|---|---|
| 7,150,726 | B2 | 12/2006 | Dalton | 7,297,151 | B2 | 11/2007 | Boecker et al. |
| 7,150,737 | B2 | 12/2006 | Purdy et al. | 7,302,295 | B2 | 11/2007 | Stahmann et al. |
| 7,150,741 | B2 | 12/2006 | Erickson et al. | 7,303,543 | B1 | 12/2007 | Maule et al. |
| 7,152,673 | B2 | 12/2006 | Lohbeck | 7,303,549 | B2 | 12/2007 | Flaherty et al. |
| 7,153,286 | B2 | 12/2006 | Busby et al. | 7,304,033 | B2 | 12/2007 | Larsen et al. |
| 7,153,823 | B2 | 12/2006 | Franco | 7,305,975 | B2 | 12/2007 | Reddy |
| 7,156,808 | B2 | 1/2007 | Quy | 7,306,555 | B2 | 12/2007 | Dolecek et al. |
| 7,156,838 | B2 | 1/2007 | Gabel et al. | 7,306,578 | B2 | 12/2007 | Gray et al. |
| 7,159,271 | B2 | 1/2007 | Sepke et al. | 7,311,693 | B2 | 12/2007 | Shekalim et al. |
| 7,162,303 | B2 | 1/2007 | Levin et al. | 7,316,700 | B2 | 1/2008 | Alden et al. |
| 7,163,385 | B2 | 1/2007 | Gharib et al. | 7,316,899 | B2 | 1/2008 | McDevitt et al. |
| 7,163,520 | B2 | 1/2007 | Bernard et al. | 7,320,675 | B2 | 1/2008 | Pastore et al. |
| 7,166,280 | B2 | 1/2007 | Franco | 7,320,677 | B2 | 1/2008 | Brouillette et al. |
| 7,187,404 | B2 | 3/2007 | Silverbrook et al. | 7,322,321 | B2 | 1/2008 | Robinson |
| 7,187,528 | B2 | 3/2007 | Talbot et al. | 7,323,141 | B2 | 1/2008 | Kirchhevel |
| 7,187,969 | B2 | 3/2007 | Willis | 7,323,543 | B2 | 1/2008 | Van Antwerp et al. |
| 7,189,352 | B2 | 3/2007 | Carpenter et al. | 7,324,012 | B2 | 1/2008 | Mann et al. |
| 7,193,521 | B2 | 3/2007 | Moberg et al. | 7,334,556 | B2 | 2/2008 | Wachigai et al. |
| 7,194,890 | B2 | 3/2007 | Tanaka et al. | 7,335,377 | B2 | 2/2008 | Stern et al. |
| 7,195,616 | B2 | 3/2007 | Diller et al. | 7,338,464 | B2 | 3/2008 | Blischak et al. |
| 7,198,603 | B2 | 4/2007 | Penner et al. | 7,341,577 | B2 | 3/2008 | Gill |
| 7,198,637 | B2 | 4/2007 | Deshmukh et al. | 7,341,581 | B2 | 3/2008 | Mallett |
| 7,198,751 | B2 | 4/2007 | Carpenter et al. | 7,344,500 | B2 | 3/2008 | Talbot et al. |
| 7,198,940 | B2 | 4/2007 | Vellinger et al. | 7,344,507 | B2 | 3/2008 | Briggs et al. |
| 7,201,319 | B2 | 4/2007 | Silverbrook et al. | 7,344,894 | B2 | 3/2008 | Greenstein et al. |
| 7,201,730 | B2 | 4/2007 | Davidner et al. | 7,347,201 | B2 | 3/2008 | Djupesland |
| 7,204,823 | B2 | 4/2007 | Estes et al. | 7,347,836 | B2 | 3/2008 | Peterson et al. |
| 7,204,958 | B2 | 4/2007 | Olsen et al. | 7,348,176 | B2 | 3/2008 | DiMilla et al. |
| 7,207,952 | B2 | 4/2007 | Takinami | 7,351,239 | B2 | 4/2008 | Gill |
| 7,207,964 | B2 | 4/2007 | Davidner et al. | 7,351,411 | B2 | 4/2008 | Holash et al. |
| 7,208,120 | B2 | 4/2007 | Bitensky et al. | 7,351,695 | B2 | 4/2008 | Almarssoo et al. |
| 7,214,207 | B2 | 5/2007 | Lynch et al. | 7,357,794 | B2 | 4/2008 | Makower et al. |
| 7,214,221 | B2 | 5/2007 | Fentress et al. | 7,357,899 | B2 | 4/2008 | Gaillard et al. |
| 7,214,658 | B2 | 5/2007 | Tobinick | 7,358,091 | B2 | 4/2008 | Phillips et al. |
| 7,217,699 | B2 | 5/2007 | Yakubov | 7,361,155 | B2 | 4/2008 | Sage, Jr. et al. |
| 7,217,796 | B2 | 5/2007 | Wang et al. | 7,362,971 | B2 | 4/2008 | Silverbrook et al. |
| 7,220,236 | B2 | 5/2007 | Pan | 7,363,072 | B2 | 4/2008 | Movahed |
| 7,220,248 | B2 | 5/2007 | Mernoe et al. | 7,363,075 | B2 | 4/2008 | Stern et al. |
| 7,220,365 | B2 | 5/2007 | Qu et al. | 7,364,566 | B2 | 4/2008 | Elkins et al. |
| 7,225,807 | B2 | 6/2007 | Papania et al. | 7,364,568 | B2 | 4/2008 | Angel et al. |
| 7,226,278 | B2 | 6/2007 | Nason et al. | 7,366,925 | B2 | 4/2008 | Keely et al. |
| 7,226,910 | B2 | 6/2007 | Wilson et al. | 7,368,003 | B2 | 5/2008 | Crapser et al. |
| 7,229,288 | B2 | 6/2007 | Stuart et al. | 7,371,418 | B2 | 5/2008 | Sheabar et al. |
| 7,232,423 | B2 | 6/2007 | Mernoe | 7,373,083 | B2 | 5/2008 | Silverbrook et al. |
| 7,232,430 | B2 | 6/2007 | Carlisle et al. | 7,373,690 | B2 | 5/2008 | Sepke et al. |
| 7,232,435 | B2 | 6/2007 | Hildebrand et al. | 7,374,544 | B2 | 5/2008 | Freeman et al. |
| 7,234,645 | B2 | 6/2007 | Silverbrook | 7,374,556 | B2 | 5/2008 | Mallett |
| 7,235,164 | B2 | 6/2007 | Anex et al. | 7,377,706 | B2 | 5/2008 | Silverbrook et al. |
| 7,235,583 | B1 | 6/2007 | Webb et al. | 7,377,907 | B2 | 5/2008 | Shekalim et al. |
| 7,237,694 | B2 | 7/2007 | Freudinger | 7,378,270 | B2 | 5/2008 | Azarnia et al. |
| 7,238,165 | B2 | 7/2007 | Vincent et al. | 7,378,443 | B2 | 5/2008 | Berge |
| 7,244,225 | B2 | 7/2007 | Loeb et al. | 7,380,447 | B2 | 6/2008 | Rollinger et al. |
| 7,244,354 | B2 | 7/2007 | Burris et al. | 7,384,413 | B2 | 6/2008 | Gross et al. |
| 7,247,428 | B2 | 7/2007 | Makrigiorgos | 7,384,912 | B2 | 6/2008 | Stewart |
| 7,247,702 | B2 | 7/2007 | Gardner et al. | 7,385,443 | B1 | 6/2008 | Denison |
| 7,250,037 | B2 | 7/2007 | Shermer et al. | 7,386,346 | B2 | 6/2008 | Struble |
| 7,251,516 | B2 | 7/2007 | Walker et al. | 7,390,311 | B2 | 6/2008 | Hildebrand et al. |
| 7,252,014 | B1 | 8/2007 | Mayer et al. | 7,390,458 | B2 | 6/2008 | Burow et al. |
| 7,252,651 | B2 | 8/2007 | Haider et al. | 7,394,182 | B2 | 7/2008 | Pelrine et al. |
| 7,256,824 | B2 | 8/2007 | Silverbrook et al. | 7,399,277 | B2 | 7/2008 | Saidara et al. |
| 7,258,864 | B2 | 8/2007 | Clark | 7,399,304 | B2 | 7/2008 | Gambale et al. |
| RE39,816 | E | 9/2007 | Stanton et al. | 7,399,602 | B2 | 7/2008 | Rush |
| 7,265,091 | B2 | 9/2007 | Lue et al. | 7,399,772 | B2 | 7/2008 | Phillips |
| 7,267,665 | B2 | 9/2007 | Steil et al. | 7,402,153 | B2 | 7/2008 | Steil et al. |
| 7,267,753 | B2 | 9/2007 | Anex et al. | 7,402,154 | B2 | 7/2008 | Holst et al. |
| 7,267,771 | B2 | 9/2007 | Gorsuch et al. | 7,407,489 | B2 | 8/2008 | Holst et al. |
| 7,268,859 | B2 | 9/2007 | Sage, Jr. et al. | 7,407,490 | B2 | 8/2008 | Bendsen et al. |
| 7,272,544 | B2 | 9/2007 | Gopal et al. | 7,410,468 | B2 | 8/2008 | Freeman et al. |
| 7,276,027 | B2 | 10/2007 | Haar et al. | 7,411,204 | B2 | 8/2008 | Appleby et al. |
| 7,276,057 | B2 | 10/2007 | Gerber | 7,416,644 | B2 | 8/2008 | Bonde |
| 7,278,983 | B2 | 10/2007 | Ireland et al. | 7,421,316 | B2 | 9/2008 | Gray et al. |
| 7,281,519 | B2 | 10/2007 | Schroeder et al. | 7,421,882 | B2 | 9/2008 | Leddy et al. |
| 7,285,293 | B2 | 10/2007 | Castillo et al. | 7,425,204 | B2 | 9/2008 | Angel et al. |
| 7,287,289 | B1 | 10/2007 | Hagopian | 7,426,408 | B2 | 9/2008 | DeNuzzio et al. |
| 7,287,485 | B2 | 10/2007 | Petrakis | 7,429,255 | B2 | 9/2008 | Thompson |
| 7,288,760 | B2 | 10/2007 | Weitz | 7,429,258 | B2 | 9/2008 | Angel et al. |
| 7,289,142 | B2 | 10/2007 | Silverbrook | 7,429,269 | B2 | 9/2008 | Schwammenthal et al. |
| 7,291,126 | B2 | 11/2007 | Shekalim et al. | 7,435,250 | B2 | 10/2008 | Francischelli et al. |
| 7,291,133 | B1 | 11/2007 | Kindler et al. | 7,435,717 | B2 | 10/2008 | Bisgaier et al. |

| Patent | Type | Date | Inventor |
|---|---|---|---|
| 7,440,806 | B1 | 10/2008 | Whitehurst et al. |
| 7,442,682 | B2 | 10/2008 | Kitaura et al. |
| RE40,570 | E | 11/2008 | Carpentier et al. |
| 7,445,616 | B2 | 11/2008 | Petrakis |
| 7,446,091 | B2 | 11/2008 | Van Den Berghe |
| 7,449,333 | B2 | 11/2008 | Rolland et al. |
| 7,452,301 | B2 | 11/2008 | Yoshioka |
| 7,455,835 | B2 | 11/2008 | Cohen et al. |
| 7,459,305 | B2 | 12/2008 | Levy |
| 7,460,152 | B2 | 12/2008 | Silverbrook et al. |
| 7,460,350 | B2 | 12/2008 | Talbot et al. |
| 7,463,934 | B2 | 12/2008 | Tronnes et al. |
| 7,464,580 | B2 | 12/2008 | Zeng et al. |
| 7,464,704 | B2 | 12/2008 | Braithwaite |
| 7,465,285 | B2 | 12/2008 | Hutchinson et al. |
| 7,465,375 | B2 | 12/2008 | Demers et al. |
| 7,467,027 | B2 | 12/2008 | Ding et al. |
| 7,467,613 | B2 | 12/2008 | Taylor, Sr. |
| 7,469,697 | B2 | 12/2008 | Lee et al. |
| 7,469,844 | B2 | 12/2008 | Conway et al. |
| 7,470,246 | B2 | 12/2008 | Mori et al. |
| 7,473,247 | B2 | 1/2009 | Mikszta et al. |
| 7,474,968 | B2 | 1/2009 | Ding et al. |
| 7,475,825 | B2 | 1/2009 | Silverbrook et al. |
| 7,476,200 | B2 | 1/2009 | Tal |
| 7,476,209 | B2 | 1/2009 | Gara et al. |
| 7,479,123 | B2 | 1/2009 | Briggs |
| 7,481,218 | B2 | 1/2009 | Djupesland |
| 7,481,759 | B2 | 1/2009 | Whitehurst et al. |
| 7,481,776 | B2 | 1/2009 | Boecker et al. |
| 7,481,792 | B2 | 1/2009 | Gonnelli et al. |
| 7,483,050 | B2 | 1/2009 | Silverbrook et al. |
| 7,483,743 | B2 | 1/2009 | Mann et al. |
| 7,485,298 | B2 | 2/2009 | Powell |
| 7,491,178 | B2 | 2/2009 | Boecker et al. |
| 7,491,187 | B2 | 2/2009 | Van Den Berghe et al. |
| 7,491,335 | B2 | 2/2009 | Reddy et al. |
| 7,493,154 | B2 | 2/2009 | Bonner et al. |
| 7,493,171 | B1 | 2/2009 | Whitehurst et al. |
| 7,497,841 | B2 | 3/2009 | Alchas |
| 7,503,903 | B2 | 3/2009 | Carlisle et al. |
| 7,507,220 | B2 | 3/2009 | Childers et al. |
| 7,507,235 | B2 | 3/2009 | Keogh et al. |
| 7,509,169 | B2 | 3/2009 | Eigler et al. |
| 7,511,914 | B2 | 3/2009 | Hiller et al. |
| 7,514,075 | B2 | 4/2009 | Hedrick et al. |
| 7,514,401 | B2 | 4/2009 | Franco |
| 7,515,060 | B2 | 4/2009 | Blomquist |
| 7,517,335 | B2 | 4/2009 | Gravesen et al. |
| 7,517,440 | B2 | 4/2009 | Anex et al. |
| 7,517,498 | B2 | 4/2009 | Fredrick |
| 7,517,530 | B2 | 4/2009 | Clark |
| 7,524,045 | B2 | 4/2009 | Silverbrook et al. |
| 7,524,287 | B2 | 4/2009 | Bharmi |
| 7,524,293 | B2 | 4/2009 | Freeman et al. |
| 7,524,304 | B2 | 4/2009 | Genosar |
| 7,530,968 | B2 | 5/2009 | Gonnelli |
| 7,530,975 | B2 | 5/2009 | Hunter |
| 7,534,221 | B2 | 5/2009 | Pile-Spellman |
| 7,534,226 | B2 | 5/2009 | Mernoe et al. |
| 7,536,983 | B2 | 5/2009 | Layher et al. |
| 7,537,571 | B2 | 5/2009 | Freeman et al. |
| 7,540,859 | B2 | 6/2009 | Claude et al. |
| 7,540,880 | B2 | 6/2009 | Nolting |
| 7,543,581 | B2 | 6/2009 | Djupesland |
| 7,547,287 | B2 | 6/2009 | Boecker et al. |
| 7,548,314 | B2 | 6/2009 | Altobelli et al. |
| 7,551,202 | B2 | 6/2009 | Silverbrook |
| 7,553,813 | B2 | 6/2009 | Unemori |
| 7,556,613 | B2 | 7/2009 | Wittmann et al. |
| 7,556,841 | B2 | 7/2009 | Kimball et al. |
| 7,558,629 | B2 | 7/2009 | Keimel et al. |
| 7,559,223 | B2 | 7/2009 | Chen et al. |
| 7,559,524 | B2 | 7/2009 | Gray et al. |
| 7,563,232 | B2 | 7/2009 | Freeman et al. |
| 7,563,255 | B2 | 7/2009 | Adamis et al. |
| 7,571,635 | B2 * | 8/2009 | Lyon .............................. 73/35.01 |
| 7,572,789 | B2 | 8/2009 | Cowen et al. |
| 7,577,477 | B2 | 8/2009 | Allen et al. |
| 7,582,063 | B2 | 9/2009 | Wurster et al. |
| 7,582,099 | B2 | 9/2009 | Freeman et al. |
| 7,584,846 | B2 | 9/2009 | Senter |
| 7,588,046 | B1 | 9/2009 | Erickson |
| 7,588,550 | B2 | 9/2009 | Leonard et al. |
| 7,588,784 | B2 | 9/2009 | Maday et al. |
| 7,589,059 | B2 | 9/2009 | Wolff et al. |
| 7,590,443 | B2 | 9/2009 | Bharmi |
| 7,591,801 | B2 | 9/2009 | Brauker et al. |
| 7,594,889 | B2 | 9/2009 | St. Ores et al. |
| 7,598,031 | B2 | 10/2009 | Liew |
| 7,602,310 | B2 | 10/2009 | Mann et al. |
| 7,603,174 | B2 | 10/2009 | De Ridder |
| 7,604,592 | B2 | 10/2009 | Freeman et al. |
| 7,604,619 | B2 | 10/2009 | Eich et al. |
| 7,605,710 | B2 | 10/2009 | Crnkovich et al. |
| 7,606,274 | B2 | 10/2009 | Mirov et al. |
| 7,606,615 | B2 | 10/2009 | Makower et al. |
| 7,607,965 | B1 | 10/2009 | Frazier |
| 7,608,640 | B2 | 10/2009 | Messadek |
| 7,615,046 | B2 | 11/2009 | Shehata |
| 7,618,615 | B2 | 11/2009 | Frey, II et al. |
| 7,618,954 | B2 | 11/2009 | Nicolau et al. |
| 7,624,409 | B2 | 11/2009 | Whymark |
| 7,625,369 | B2 | 12/2009 | Abboud et al. |
| 7,628,590 | B2 | 12/2009 | Jacobsen et al. |
| 7,628,772 | B2 | 12/2009 | McConnell et al. |
| 7,632,228 | B2 | 12/2009 | Brauker et al. |
| 7,632,247 | B2 | 12/2009 | Adams |
| 7,632,248 | B2 | 12/2009 | Delk et al. |
| 7,635,575 | B2 | 12/2009 | Scherze et al. |
| 7,637,931 | B2 | 12/2009 | Heaton |
| 7,638,095 | B2 | 12/2009 | Sabol |
| 7,642,232 | B2 | 1/2010 | Green et al. |
| 7,644,203 | B2 | 1/2010 | Ingles |
| 7,645,253 | B2 | 1/2010 | Gura et al. |
| 7,647,107 | B2 | 1/2010 | Warman et al. |
| 7,647,115 | B2 | 1/2010 | Levin et al. |
| 7,647,237 | B2 | 1/2010 | Malave et al. |
| 7,650,181 | B2 | 1/2010 | Freeman et al. |
| 7,650,190 | B2 | 1/2010 | Zhou et al. |
| 7,651,489 | B2 | 1/2010 | Estes et al. |
| 7,651,868 | B2 | 1/2010 | McDevitt et al. |
| 7,653,639 | B2 | 1/2010 | Classen |
| 7,654,127 | B2 | 2/2010 | Krulevitch et al. |
| 7,654,131 | B2 | 2/2010 | Ascheman |
| 7,654,484 | B2 | 2/2010 | Mogensen et al. |
| 7,654,976 | B2 | 2/2010 | Peterson et al. |
| 7,654,982 | B2 | 2/2010 | Carlisle et al. |
| 7,655,221 | B2 | 2/2010 | Rasmussen et al. |
| 7,657,313 | B2 | 2/2010 | Rom |
| 7,662,105 | B2 | 2/2010 | Hatlestad |
| 7,662,140 | B2 | 2/2010 | Heruth et al. |
| 7,662,558 | B2 | 2/2010 | Liew |
| 7,674,243 | B2 | 3/2010 | Dacquay et al. |
| 7,674,485 | B2 | 3/2010 | Bhaskaran et al. |
| 7,676,263 | B2 | 3/2010 | Harris et al. |
| 7,678,071 | B2 | 3/2010 | Lebel et al. |
| 7,678,761 | B2 | 3/2010 | Coleman |
| 7,678,762 | B2 | 3/2010 | Green et al. |
| 7,678,763 | B2 | 3/2010 | Green et al. |
| 7,678,772 | B2 | 3/2010 | Jia et al. |
| 7,678,833 | B2 | 3/2010 | Ott |
| 7,682,430 | B2 | 3/2010 | Kraemer et al. |
| 7,682,563 | B2 | 3/2010 | Carpenter et al. |
| 7,683,029 | B2 | 3/2010 | Hindle et al. |
| 7,685,865 | B2 | 3/2010 | Norenberg |
| 7,687,272 | B1 | 3/2010 | Buchwald et al. |
| RE41,288 | E | 4/2010 | Coolidge et al. |
| 7,691,330 | B1 | 4/2010 | Winkler et al. |
| 7,695,627 | B2 | 4/2010 | Bosch et al. |
| 7,697,995 | B2 | 4/2010 | Cross, Jr. et al. |
| 7,699,767 | B2 | 4/2010 | Mueth et al. |
| 7,699,833 | B2 | 4/2010 | Moberg et al. |
| 7,704,226 | B2 | 4/2010 | Mueller, Jr. et al. |
| 7,704,227 | B2 | 4/2010 | Moberg et al. |
| 7,708,717 | B2 | 5/2010 | Estes et al. |
| 7,708,872 | B2 | 5/2010 | Eidsned et al. |
| 7,708,915 | B2 | 5/2010 | Castor |

| Patent/Publication | Date | Inventor |
|---|---|---|
| 7,713,240 B2 | 5/2010 | Istoc et al. |
| 7,713,262 B2 | 5/2010 | Adams et al. |
| 7,714,757 B2 | 5/2010 | Denison et al. |
| 7,714,889 B2 | 5/2010 | Silverbrook |
| 7,715,917 B2 | 5/2010 | Chinchoy et al. |
| 7,716,964 B2 | 5/2010 | Kurtz et al. |
| 7,717,856 B2 | 5/2010 | Chen et al. |
| 7,717,871 B2 | 5/2010 | Odland |
| 7,717,903 B2 | 5/2010 | Estes et al. |
| 7,726,955 B2 | 6/2010 | Ryser et al. |
| 7,727,181 B2 | 6/2010 | Rush |
| 7,771,414 B2 | 8/2010 | Trieu |
| 7,811,279 B2 | 10/2010 | John |
| 7,914,499 B2 | 3/2011 | Gonneli et al. |
| 7,922,096 B2 | 4/2011 | Eilersen |
| 7,931,864 B2 | 4/2011 | Kloepfer et al. |
| 7,935,079 B2 | 5/2011 | Ludin et al. |
| 7,955,305 B2 | 6/2011 | Moberg et al. |
| 7,981,076 B2 | 7/2011 | Sullivan et al. |
| 2001/0000282 A1 | 4/2001 | Poleshuk et al. |
| 2002/0004015 A1 | 1/2002 | Carlisle et al. |
| 2002/0018720 A1 | 2/2002 | Carlisle et al. |
| 2002/0019714 A1 | 2/2002 | Carlisle et al. |
| 2002/0040208 A1 | 4/2002 | Flaherty et al. |
| 2002/0045265 A1 | 4/2002 | Bergh et al. |
| 2002/0048536 A1 | 4/2002 | Bergh et al. |
| 2002/0055787 A1 | 5/2002 | Lennox et al. |
| 2002/0059959 A1 | 5/2002 | Qatu et al. |
| 2002/0117214 A1 | 8/2002 | Tucker et al. |
| 2002/0120234 A1 | 8/2002 | Kong |
| 2002/0154571 A1 | 10/2002 | Cefai et al. |
| 2003/0014016 A1 | 1/2003 | Purdy |
| 2003/0036725 A1 | 2/2003 | Lavi et al. |
| 2003/0055380 A1 | 3/2003 | Flaherty |
| 2003/0060765 A1 | 3/2003 | Campbell et al. |
| 2003/0093105 A1 | 5/2003 | Huffmaster |
| 2003/0097082 A1 | 5/2003 | Purdy et al. |
| 2003/0130577 A1 | 7/2003 | Purdy et al. |
| 2003/0183289 A1 | 10/2003 | Seuret et al. |
| 2003/0212364 A1 | 11/2003 | Mann et al. |
| 2003/0216683 A1 | 11/2003 | Shekalim |
| 2004/0010207 A1 | 1/2004 | Flaherty et al. |
| 2004/0051368 A1 | 3/2004 | Caputo |
| 2004/0078028 A1 | 4/2004 | Flaherty et al. |
| 2004/0092865 A1 | 5/2004 | Flaherty et al. |
| 2004/0116866 A1 | 6/2004 | Gorman et al. |
| 2004/0116905 A1 | 6/2004 | Pederson et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0167478 A1 | 8/2004 | Mooney et al. |
| 2004/0171987 A1 | 9/2004 | Bridle et al. |
| 2004/0193090 A1 | 9/2004 | Lebel et al. |
| 2004/0204673 A1 | 10/2004 | Flaherty |
| 2004/0220551 A1 | 11/2004 | Flaherty et al. |
| 2004/0225252 A1 | 11/2004 | Gillespie et al. |
| 2004/0235446 A1 | 11/2004 | Flaherty et al. |
| 2004/0260233 A1 | 12/2004 | Garibotto et al. |
| 2005/0020980 A1 | 1/2005 | Inoue et al. |
| 2005/0022274 A1 | 1/2005 | Campbell et al. |
| 2005/0038379 A1 | 2/2005 | Beebe et al. |
| 2005/0043710 A1 | 2/2005 | Hadzic et al. |
| 2005/0054994 A1 | 3/2005 | Cioanta et al. |
| 2005/0060030 A1 | 3/2005 | Lashinski et al. |
| 2005/0115622 A1 | 6/2005 | Bennett et al. |
| 2005/0137530 A1 | 6/2005 | Campbell et al. |
| 2005/0137578 A1 | 6/2005 | Heruth et al. |
| 2005/0171512 A1 | 8/2005 | Flaherty |
| 2005/0171513 A1 | 8/2005 | Mann et al. |
| 2005/0171569 A1 | 8/2005 | Girard et al. |
| 2005/0182366 A1 | 8/2005 | Vogt et al. |
| 2005/0211322 A1 | 9/2005 | Lohbeck |
| 2005/0238507 A1 | 10/2005 | Dilanni et al. |
| 2005/0240119 A1 | 10/2005 | Draudt et al. |
| 2005/0245867 A1 | 11/2005 | Olsen et al. |
| 2006/0041229 A1 | 2/2006 | Garibotto et al. |
| 2006/0042695 A1 | 3/2006 | Gonia |
| 2006/0116757 A1 | 6/2006 | Lashinski et al. |
| 2006/0139354 A1 | 6/2006 | Suma |
| 2006/0149214 A1 | 7/2006 | Breiter et al. |
| 2006/0150747 A1 | 7/2006 | Mallett |
| 2006/0178633 A1 | 8/2006 | Garibotto et al. |
| 2006/0189895 A1 | 8/2006 | Neel et al. |
| 2006/0206029 A1 | 9/2006 | Yair |
| 2006/0206054 A1 | 9/2006 | Shekalim et al. |
| 2006/0243804 A1 | 11/2006 | Cristoffersen et al. |
| 2006/0264835 A1 | 11/2006 | Nielson et al. |
| 2006/0282290 A1 | 12/2006 | Flaherty et al. |
| 2007/0000337 A1 | 1/2007 | Gross |
| 2007/0033074 A1 | 2/2007 | Nitzan et al. |
| 2007/0100235 A1 | 5/2007 | Kennedy |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0142822 A1 | 6/2007 | Remde |
| 2007/0149926 A1 | 6/2007 | Moberg et al. |
| 2007/0150019 A1 | 6/2007 | Youker et al. |
| 2007/0156092 A1 | 7/2007 | Estes et al. |
| 2007/0161955 A1 | 7/2007 | Bynum et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2007/0201992 A1 | 8/2007 | Mernoe et al. |
| 2007/0203459 A1 | 8/2007 | Mernoe et al. |
| 2007/0219496 A1 | 9/2007 | Kamen et al. |
| 2007/0250007 A1 | 10/2007 | Shekalim et al. |
| 2007/0264130 A1 | 11/2007 | Mallett |
| 2007/0287985 A1 | 12/2007 | Estes et al. |
| 2007/0288176 A1 | 12/2007 | Carlisle et al. |
| 2008/0004601 A1 | 1/2008 | Jennewine et al. |
| 2008/0015510 A1 | 1/2008 | Sandoz et al. |
| 2008/0029173 A1 | 2/2008 | DiPerna |
| 2008/0033357 A1 | 2/2008 | Mann et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0082040 A1 | 4/2008 | Kubler et al. |
| 2008/0092969 A1 | 4/2008 | DiPerna |
| 2008/0097291 A1 | 4/2008 | Hanson et al. |
| 2008/0097375 A1 | 4/2008 | Bikovsky |
| 2008/0114228 A1 | 5/2008 | McCloskey et al. |
| 2008/0116647 A1 | 5/2008 | Anderson et al. |
| 2008/0147004 A1 | 6/2008 | Mann et al. |
| 2008/0147050 A1 | 6/2008 | Mann et al. |
| 2008/0160492 A1 | 7/2008 | Campbell et al. |
| 2008/0196762 A1 | 8/2008 | Mallett et al. |
| 2008/0197801 A1 | 8/2008 | Manor et al. |
| 2008/0281276 A1 | 11/2008 | Shekalim et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0304365 A1 | 12/2008 | Jarvis et al. |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0088701 A1 | 4/2009 | Larsen |
| 2009/0131863 A1 | 5/2009 | Carlisle et al. |
| 2009/0143732 A1 | 6/2009 | O'Connor et al. |
| 2009/0156990 A1 | 6/2009 | Wenger et al. |
| 2009/0191067 A1 | 7/2009 | DiPierna |
| 2009/0217982 A1 | 9/2009 | DiPerna |
| 2009/0229374 A1 | 9/2009 | Carlisle et al. |
| 2009/0234594 A1 | 9/2009 | Carlisle et al. |
| 2009/0247982 A1 | 10/2009 | Krulevitch et al. |
| 2009/0272928 A1 | 11/2009 | Alvarez et al. |
| 2009/0275887 A1 | 11/2009 | Estes et al. |
| 2009/0287180 A1 | 11/2009 | DiPerna |
| 2009/0292245 A1 | 11/2009 | Basso et al. |
| 2009/0321675 A1 | 12/2009 | Alvarez et al. |
| 2010/0008795 A1 | 1/2010 | DiPerna |
| 2010/0032041 A1 | 2/2010 | DiPerna |

| | | | |
|---|---|---|---|
| 2010/0036327 A1 | 2/2010 | DiPerna | |
| 2010/0038572 A1 | 2/2010 | Alvarez et al. | |
| 2010/0043738 A1 | 2/2010 | Grandvallet et al. | |
| 2010/0049164 A1 | 2/2010 | Estes et al. | |
| 2010/0063765 A1 | 3/2010 | Carlisle et al. | |
| 2010/0065579 A1 | 3/2010 | DiPerna | |
| 2010/0069890 A1 | 3/2010 | Graskov et al. | |
| 2010/0071446 A1 | 3/2010 | Brown | |
| 2010/0081993 A1 | 4/2010 | O'Connor | |
| 2010/0094251 A1 | 4/2010 | Estes et al. | |
| 2010/0096019 A1 | 4/2010 | DiPerna | |
| 2010/0106100 A1 | 4/2010 | Petersen | |
| 2010/0121306 A1 | 5/2010 | Yodfat et al. | |
| 2010/0137833 A1 | 6/2010 | Glynn | |
| 2010/0145303 A1 | 6/2010 | Yodfat et al. | |
| 2010/0165795 A1 | 7/2010 | Elder et al. | |
| 2010/0168711 A1 | 7/2010 | Bazargan et al. | |
| 2010/0198183 A1 | 8/2010 | Lanigan et al. | |
| 2010/0218586 A1 | 9/2010 | Rosinko | |
| 2010/0228186 A1 | 9/2010 | Estes et al. | |
| 2010/0249566 A1 | 9/2010 | Suess et al. | |
| 2011/0009813 A1 | 1/2011 | Rankers | |
| 2011/0033833 A1 | 2/2011 | Blomquist | |
| 2011/0050428 A1 | 3/2011 | Istoc | |
| 2011/0108158 A1 | 5/2011 | Huwiler et al. | |
| 2011/0111794 A1 | 5/2011 | Bochenko | |
| 2011/0124996 A1 | 5/2011 | Reinke et al. | |
| 2011/0152769 A1 | 6/2011 | Ramey et al. | |

FOREIGN PATENT DOCUMENTS

| | | |
|---|---|---|
| CN | 2668847 Y | 1/2005 |
| EP | 0055836 | 7/1982 |
| EP | 0376894 | 12/1988 |
| EP | 0385916 | 5/1990 |
| EP | 0494042 | 7/1992 |
| EP | 0560571 | 9/1993 |
| EP | 1217275 | 12/2000 |
| EP | 1938750 | 7/2008 |
| JP | 06-016165 | 4/1994 |
| JP | 08-312820 | 11/1996 |
| JP | 2952037 | 9/1999 |
| JP | 2002-143293 | 5/2002 |
| JP | 2006-009944 | 1/2006 |
| JP | 2006-101985 | 4/2009 |
| JP | 2009-148591 | 7/2009 |
| JP | 2010-075736 | 4/2010 |
| KR | 10-2001-0080519 | 8/2001 |
| WO | WO 90/13795 | 11/1990 |
| WO | WO 91/00753 | 1/1991 |
| WO | WO 94/26329 | 11/1994 |
| WO | WO 95/32013 | 11/1995 |
| WO | WO 96/08049 | 3/1996 |
| WO | WO 96/25189 | 8/1996 |
| WO | WO 98/19627 | 5/1998 |
| WO | WO 98/57683 | 12/1998 |
| WO | WO 99/01088 | 1/1999 |
| WO | WO 00/10628 | 3/2000 |
| WO | WO 00/35527 | 6/2000 |
| WO | WO 00/40346 | 7/2000 |
| WO | WO 00/72900 | 12/2000 |
| WO | WO 01/30422 | 5/2001 |
| WO | WO 02/028532 | 10/2001 |
| WO | WO 02/11791 | 2/2002 |
| WO | WO 02/26102 | 4/2002 |
| WO | WO 03/081052 | 3/2003 |
| WO | WO 03/102737 | 6/2003 |
| WO | WO 2004/009152 | 1/2004 |
| WO | WO 2004/088148 | 3/2004 |
| WO | WO 2004/036150 | 4/2004 |
| WO | WO 2004/047677 | 6/2004 |
| WO | WO 2004/060464 | 7/2004 |
| WO | WO 2004/056412 | 12/2004 |
| WO | WO 2005/082450 | 2/2005 |
| WO | WO 2005/018507 | 3/2005 |
| WO | WO 2006/108219 | 10/2006 |
| WO | WO 2007/038059 | 4/2007 |
| WO | WO 2007/038060 | 4/2007 |
| WO | WO 2007/038091 | 4/2007 |
| WO | WO 2007/056504 | 5/2007 |
| WO | WO 2007/056592 | 5/2007 |
| WO | WO 2007/089983 | 8/2007 |
| WO | WO 2007/098265 | 8/2007 |
| WO | WO 2007/098287 | 8/2007 |
| WO | WO 2007/106232 | 9/2007 |
| WO | WO 2007/119149 | 10/2007 |
| WO | WO 2008/071220 | 3/2008 |
| WO | WO 2008/144693 | 5/2008 |
| WO | WO 2008/144695 | 5/2008 |
| WO | WO 2008/144697 | 5/2008 |
| WO | WO 2008/144698 | 5/2008 |
| WO | WO 2008/103175 | 8/2008 |
| WO | WO 2008/028509 | 9/2008 |
| WO | WO 2008/037270 | 9/2008 |
| WO | WO 2008/037271 | 9/2008 |
| WO | WO 2008/037272 | 9/2008 |
| WO | WO 2008/037273 | 9/2008 |
| WO | WO 2008/043381 | 10/2008 |
| WO | WO 2008/050126 | 10/2008 |
| WO | WO 2008/050128 | 10/2008 |
| WO | WO 2008/121599 | 10/2008 |
| WO | WO 2009/106233 | 2/2009 |
| WO | WO 2009/032402 | 7/2009 |
| WO | WO 2009/035759 | 7/2009 |
| WO | WO 2009/035761 | 7/2009 |
| WO | WO 2009/035762 | 7/2009 |
| WO | WO 2009/094590 | 7/2009 |
| WO | WO 2009/108639 | 9/2009 |
| WO | WO 2009/032399 | 10/2009 |
| WO | WO 2009/032400 | 10/2009 |
| WO | WO 2009/035753 | 10/2009 |
| WO | WO 2009/143188 | 11/2009 |
| WO | WO 2010/016977 | 2/2010 |
| WO | WO 2010/016978 | 2/2010 |
| WO | WO 2010/033634 | 3/2010 |
| WO | WO 2010/033878 | 3/2010 |
| WO | WO 2010/038031 | 4/2010 |
| WO | WO 2010/096449 | 8/2010 |
| WO | WO 2010/099490 | 9/2010 |
| WO | WO 2011/014704 | 2/2011 |
| WO | WO 2011/017667 | 2/2011 |

OTHER PUBLICATIONS

International Search Report and Written Opinion mailed on Sep. 10, 2004 in International Application: PCT/US2003/022703 filed on Jul. 15, 2003 and published as: WO 04/009152 on Jan. 29, 2004.

International Search Report and Written Opinion mailed on: Jul. 23, 2007 in International Application: PCT/2007/060633 filed on: Jan. 17 2007 and published as: WO 07/089983 on: Aug. 9, 2007.

International Preliminary Report on Patentability mailed on: Jul. 29, 2008 in International Application: PCT/2007/060633 filed on: Jan. 17, 2007 and published as: WO 07/089983 on: Aug. 9, 2007.

International Search Report and Written Opinion mailed on: May 29, 2009 in International Application: PCT/US2009/035022 filed on: Jan. 23, 2009 and published as: WO 09/108639 on: Sep. 3, 2009.

International Preliminary Report on Patentability mailed on: Sep. 10, 2010 in International Application: PCT/US2009/035022 filed on: Jan. 23, 2009 and published as: WO 09/108639 on: Sep. 3, 2009.

International Preliminary Report on Patentability mailed on: Oct. 6, 2009 in International Application: PCT/2008/058044 filed on: Mar. 24, 2008 and published as: WO 08/121599 on: Oct. 9, 2009.

Written Opinion of the International Searching Authority of Aug. 11, 2008 in International Application: PCT/US2008/058044 filed on: Mar. 24, 2008 and published as: WO 08/121599 on: Oct. 9, 2009.

International Search Report and Written Opinion mailed on Feb. 17, 2011 in International Application: PCT/US2009/049110 filed on: Jun. 29, 2009 and published as: WO 10/016977 on: Feb. 11, 2010.

International Search Report and Written Opinion mailed on: Jan. 27, 2010 in International Application: PCT/US2009/049110 filed on: Jun. 29, 2009 and published as: WO 10/016977 on: Feb. 11, 2010.

International Search Report and Written Opinion mailed on: Feb. 17, 2011 in International Application: PCT/2009/049166 filed on: Jun. 29, 2009 and published as: WO 10/016978 on: Feb. 11, 2010.

International Search Report and Written Opinion mailed on: Feb. 4, 2010 in International Application: PCT/2009/049166 filed on: Jun. 29, 2009 and published as: WO 10/016978 on: Feb. 11, 2010.

International Preliminary Report on Patentability mailed on Aug. 5, 2010 in International Application: PCT/US2009/031906 filed on Jan. 23, 2009 and published as: WO 09/094590 on Jul. 30, 2009.
International Search Report and Written Opinion mailed on Jul. 28, 2009 in International Application: PCT/US2009/031906 filed on Jan. 23, 2009 and published as: WO 09/094590 on Jul. 30, 2009.
International Search Report and Written Opinion mailed on: Apr. 27, 2011 in International Application: PCT/US2010/044789 filed on Aug. 6, 2011 and published as: WO 11/017667 on Feb. 10, 2011.
International Search Report and Written Opinion mailed on: Jan. 4, 2010 in International Application: PCT/US2009/044569 filed on: May 19, 2009 and published as: WO 09/143188 on: Nov. 26, 2009.
International Preliminary Report on Patentability mailed: Dec. 2, 2010, in International Patent Application No. PCT/US2009/044569 filed on: May 19, 2009 and published as WO 2009/143188 on: Nov. 26, 2009.
International Preliminary Report on Patentability mailed on Mar. 31, 2011 in International Application: PCT/2009/057208 filed on: Sep. 16, 2009 and published as: WO 10/033634 on: Mar. 25, 2010.
International Search Report and Written Opinion mailed on Apr. 1, 2010 in International Application: PCT/2009/057208 filed on: Sep. 16, 2009 and published as: WO 10/033634 on: Mar. 25, 2010.
International Search Report and Written Opinion mailed on: Sep. 30, 2010 in International Application: PCT/2010/025663 filed on: Feb. 26, 2010 and published as: WO 10/099490 on: Sep. 2, 2010.
International Preliminary Report on Patentability mailed on Mar. 31, 2011 in International Application: PCT/2009/57591 filed on: Sep. 18, 2009 and published as: WO 10/033878 on: Mar. 25, 2010
International Search Report and Written Opinion mailed on Apr. 12, 2010 in International Application: PCT/2009/57591 filed on: Sep. 18, 2009 and published as: WO 10/033878 on: Mar. 25, 2010.
International Search Report and Written Opinion mailed on Apr. 11, 2011 in International Application: PCT/2010/034789 filed on: Jul. 29, 2010 and published as: WO 11/014704 on: Feb. 3, 2011.
Office Action mailed on: Dec. 15, 2005 in U.S. Appl. No. 10/200,109, filed May 4, 2007 and issued as: 7,008,403 on: Mar. 7, 2007.
Office Action mailed on: Apr. 14, 2005 in U.S. Appl. No. 10/200,109, filed May 4, 2007 and issued as: 7,008,403 on: Mar. 7, 2007.
Office Action mailed on: Oct. 4, 2004 in U.S. Appl. No. 10/200,109, filed May 4, 2007 and issued as: 7,008,403 on: Mar. 7, 2007.
Office Action mailed on: Jun. 23, 2004 in U.S. Appl. No. 10/200,109, filed May 4, 2007 and issued as: 7,008,403 on: Mar. 7, 2007.
Office Action mailed on: May 29, 2009 in U.S. Appl. No. 11/744,819, filed May 4, 2007 and published as: US-2007-0264130 on Nov. 15, 2007.
Office Action mailed on: Aug. 5, 2009 in U.S. Appl. No. 11/744,819, filed May 4, 2007 and published as: US-2007-0264130 on Nov. 15, 2007.
Office Action mailed on: Mar. 9, 2010 in U.S. Appl. No. 11/744,819, filed May 4, 2007 and published as: US-2007-0264130 on Nov. 15, 2007.
Office Action mailed on: Jan. 8, 2008 in U.S. Appl. No. 11/342,015, filed Jan. 27, 2006 and published as: US-2006-0150747 on: Jul. 13, 2006 and issued as: 7,341,581 on: Mar. 11, 2008.
Office Action mailed on: Jun. 8, 2007 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 11, 2008 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 3, 2011 in U.S. Appl. No. 12/020,498, filed Jan. 25, 2008 and published as: US-2009-0191067 on: Jul. 30, 2009.
Office Action mailed on: Jul. 18, 2011 in U.S. Appl. No. 12/108,462, filed Apr. 23, 2008 and published as: US-2008-0196762 on: Aug. 21, 2008.
Office Action mailed on: Mar. 21, 2011 in U.S. Appl. No. 12/108,462, filed Apr. 23, 2008 and published as: US-2008-0196762 on: Aug. 21, 2008.
Office Action mailed on: Oct. 6, 2010 in U.S. Appl. No. 12/108,462, filed Apr. 23, 2008 and published as: US-2008-0196762 on: Aug. 21, 2008.
Office Action mailed on Dec. 29, 2009 in U.S. Appl. No. 12/486,795, filed May 19, 2009 and published as US 2009/0287180 on Nov. 19, 2009.
Office Action mailed on May 27, 2010 in U.S. Appl. No. 12/486,795, filed May 19, 2009 and published as US 2009/0287180 on Nov. 19, 2009.

* cited by examiner

FLOW REGULATING STOPCOCKS AND RELATED METHODS

RELATED APPLICATIONS

This application claims the Paris Convention priority and incorporates by reference U.S. Provisional Patent Application Ser. No. 61/097,492, filed Sep. 16, 2008 and entitled "Flow Regulating Stopcocks and Related Methods."

BACKGROUND

This disclosure relates to devices and methods for the regulation of the flow of flow materials, as well as features to prevent undesired flow.

SUMMARY

A novel enhanced stopcock is disclosed, as well as related methods, that safely controls flow of flow materials from a pump. A pump fills a stopcock, which then dispenses to a target. Flow material is dispensed from the second chamber when the stopcock is moved to a different position wherein it is no longer in fluid communication with the first chamber. Pressure sensors disposed in fluid communication with first and second chambers are used to determine a volume of flow material dispensed.

According to a feature of the present disclosure, a device is disclosed comprising a stopcock device having a first chamber, a first compressible member disposed in the first chamber, a stopcock having a second chamber for holding aliquots of flow material to be dispensed, a second compressible member disposed in the second chamber, and a first pressure sensor. The second chamber is filled with flow material from first chamber when stopcock is in a first position and the stopcock device only dispenses flow material when the stopcock is in the second position that is not in fluid communication with the first chamber.

According to a feature of the present disclosure, a method is disclosed comprising providing a stopcock device having a first chamber, a first compressible member disposed in the first chamber, a stopcock having a second chamber for holding aliquots of flow material to be dispensed, a second compressible member disposed in the second chamber, and a first pressure sensor. The second chamber is filled with flow material from first chamber when stopcock is in a first position and the stopcock device only dispenses flow material when the stopcock is in the second position that is not in fluid communication with the first chamber.

According to a feature of the present disclosure, a method is disclosed comprising positioning a stopcock into a first position whereby a first chamber and a second chamber are in fluid communication, positioning the stopcock into a second position whereby the first chamber and the second chamber are not in fluid communication and whereby the second chamber is in fluid communication with a dispensing conduit, measuring the pressure in the second chamber with a first pressure sensor; and calculating the flow rate in about real time.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
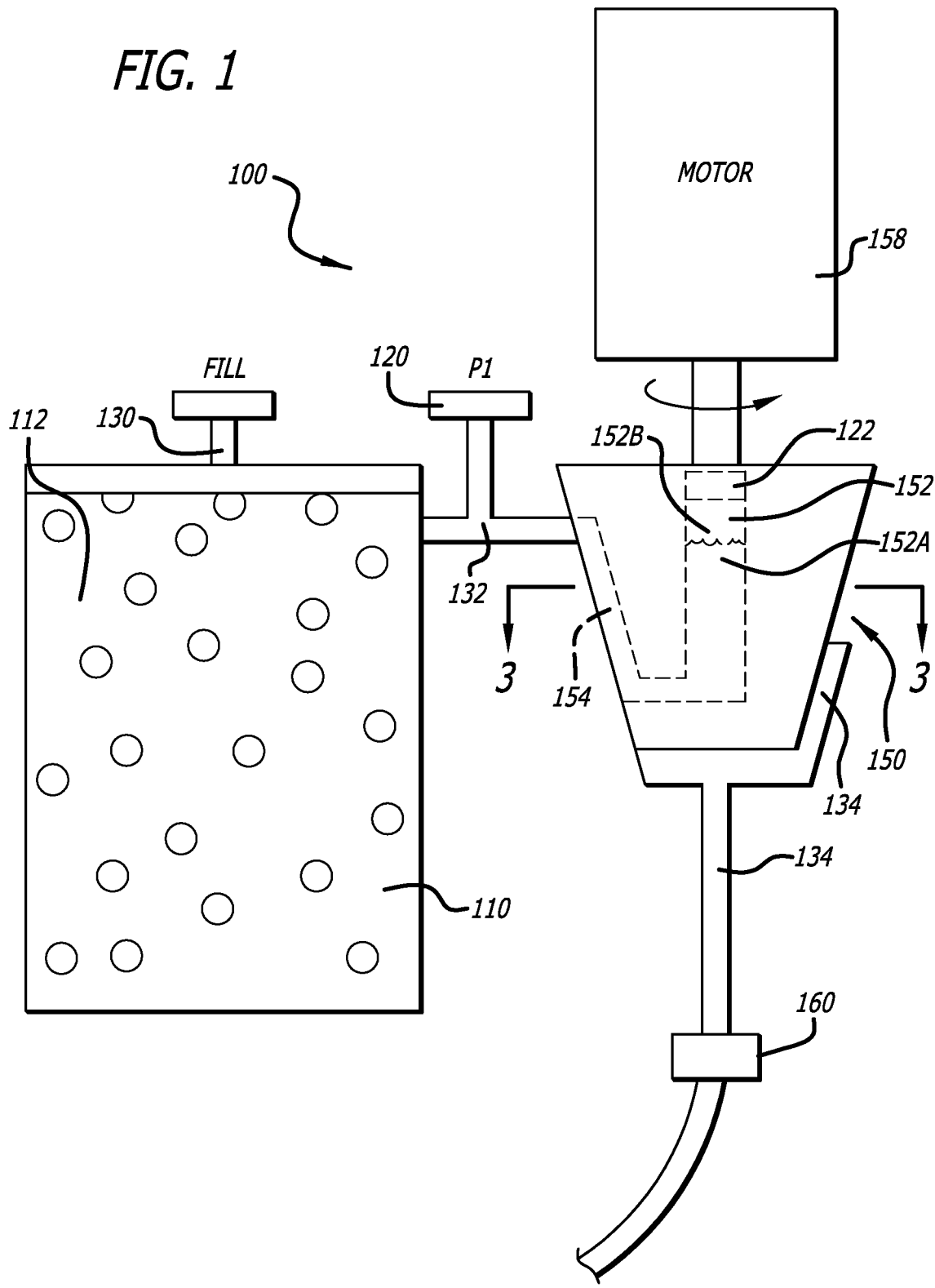
FIG. 1 is a schematic view of an embodiment of the stopcock device of the present disclosure.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

As used herein, the term "compressible member" shall be understood to mean devices that cause a gas or fluid to be compressed when a gas or fluid is placed into a chamber where the compressible member is disposed. Examples of compressible members include, for example, closed cell foams, elastomeric diaphragms, pistons, and secondary chambers charged with a fixed volume of gas, wherein when a gas or fluid is placed into the chamber in which the compressible member is disposed, the gas or fluid in the compressible member compresses.

The present inventor has discovered a device and method for preventing inadvertent flow of flow materials from a pump. The device comprises a stopcock having a chamber built in that is charged with aliquots of flow material. The stopcock is moved from a first position that is used for charging (filling) the stopcock into at least a second position that is configured for dispensing the stored aliquots of flow material.

One or more pressure sensors are disposed to measure, in real time, the pressure of the chambers holding the flow materials, thereby deriving the volume of flow material dispensed from the stopcock device. Because flow volumes and the elapsed time are also know, the flow rate of the dispensed flow material may be calculated, according to embodiments. Temperature sensors may similarly be disposed to improve the accuracy of the calculations used to measure the flow volume or rate.

According to embodiments, stopcock device 100 is illustrated generally in FIG. 1. Stopcock device 100 comprises first chamber 110, stopcock 150, and conduits placing first chamber 110 and stopcock 150 into fluid communication and allowing for dispensing of the flow material. Stopcock is connected to positioning device 158, which positions stopcock 150 into one of a plurality of positions for at least charging chambers within stopcock with flow material and into position for dispensing flow material. Within stopcock 150 is at least one second chamber 152 and corresponding second chamber conduit 154. According to embodiments, first pressure sensor 120 and second pressure sensor 122 are disposed at locations in stopcock device 100 that allow for the accurate measurement of the pressure of first chamber 110 and second chamber 152, thereby allowing calculation of flow volume and flow rates of flow materials based on change of pressure calculations, as described in detail below.

A computer performs the relevant calculations. The computer comprises at least a timing device for measuring elapsed time, which may comprise a clock or a timer, for example; devices to receive input from the pressure sensors, temperature sensors, and users; and a processor for performing the calculations disclosed herein.

First chamber 110 is a chamber of known volume. According to embodiments, first chamber 110 volume comprises first chamber 110 and first chamber/stopcock conduit 132. According to embodiments, first pressure sensor 120 is disposed such that it is in at least gas communication with first chamber 110 or first chamber/stopcock conduit 132, depending on the components of the present disclosure comprising first chamber 110. Fill conduit 130 comprises a conduit for filling first chamber 110 with a flow material. Conduits may comprise any conventional device used to sealably transport gases or flow materials, for example pipes, tubes, or other conduits defined by a sealed body terminating in one or more open ends through which a flow material or gas enters and exits the interior of the sealed body.

According to embodiments, first chamber 110 comprises a chamber having a quantity of gas contained in a compressible member. Filling of first chamber 110 does not displace gas; in other words, the net number of gas molecules remains constant as flow material fills first chamber 110, thereby pressurizing the gas as the volume of the gas decreases. This may be accomplished by installing a one way valve, such as a check valve, as part of fill conduit 130. The exact amount of gas does not need to be known, provided the differential pressure can be measured and the total volume of first chamber is known.

According to embodiments, gas in first chamber 110 may be contained in a secondary chamber (i.e., the compressible member). The secondary chamber comprises, according to various embodiments, a gas "pillow" formed from a flexible diaphragm that compresses when flow material fills first chamber 110; a movable, sealed divider (e.g., a piston) that compresses when flow material fills first chamber 110, etc. According to embodiments, gas may also be contained in a closed cell foam that occupies substantially all or part of first chamber 110.

In each of these embodiments, the compressed gas will exert pressure on the flow material whereby flow material will flow into second chamber 152, as described below. According to embodiments, in addition to, or instead of pressure, gravity or a pump such as a lead screw may be used to move flow material from first chamber to second chamber 152, as described below.

According to embodiments and as illustrated in FIG. 1, first chamber 110 has disposed therein compressible member 112. According to embodiments, compressible member 112 comprises closed cell foam. Compressible member 112 may also comprise rubber or another compressible material that effects a differential gas pressure in first chamber 110 when first chamber 110 is charged with flow material verses when first chamber 110 is not charged with flow material. According to embodiments, compressible member 112 comprises a pocket of air contained within a compressible bag or "pillow." According to embodiments, compressible member is disposed in first chamber 110 to ensure sufficient pressure to move the last amount of flow material from first chamber 110 to second chamber 152.

According to other embodiments, compressible member is not used, as described above. Indeed, as flow material is put into first chamber 110, the flow material is under pressure or delivered through a one-way valve. Thus, flow material will naturally flow from first chamber 110 to second chamber 152 due to the pressure exerted by the gas that is pressurized as first chamber 110 is filled.

Because the gas or closed cell foam will tend to equalize as flow material moves out of first chamber, the last amount of flow material will be difficult to remove. Removal of this last amount of flow material may be accomplished by placing the gas in first chamber 110 under pressure initially, according to embodiments. According to other embodiments, closed cell foam will mechanically tend to remove this last amount of flow material in much the same way as the foam relaxes into substantially the entire chamber as the flow material flows out. Finally, gravity or a pumping mechanism may be used to remove the last amount of flow material.

According to embodiments, stopcock device 100 is disposed along a flow path to prevent flow of a flow material except in pre-determined configurations. Stopcocks are well known and understood by artisans, and include any generic two- or three-way valves, for example. According to embodiments, stopcock 150 comprises second chamber 152, which is a cavity disposed within stopcock 150 and second chamber conduit 154, which provides fluid communication between second chamber 152 and other components of stopcock device 100, as detailed herein. According to embodiments, second chamber conduit 154 comprises a plurality of conduits or chambers, whereby the fluid/gas communication features of the present disclosure connect with the different conduits or chambers. According to other embodiments, second chamber conduit 154 is a single conduit wherein each connecting conduit is situated to articulate with second chamber conduit 154 in substantially the same location relative to stopcock 150 depending on the position of stopcock 150.

Within second chamber 152, the amount of gas is constant like with first chamber 110, and need not be known. The same devices may be used in second chamber with respect to the gas compressible member or secondary chambers may be configured with one or more one-way valves for the filling and dispensing of flow material to prevent back flow, as would be known and understood by artisans. For example, and according to embodiments, second chamber 152 likewise has disposed therein compressible member, such as a closed cell foam. Like compressible member 112, compressible member compresses when charged with flow material, thereby creating a pressure differential in second chamber 152 when second chamber 152 is charged with flow material versus when second chamber 152 is not charged with flow material.

Figure 2:
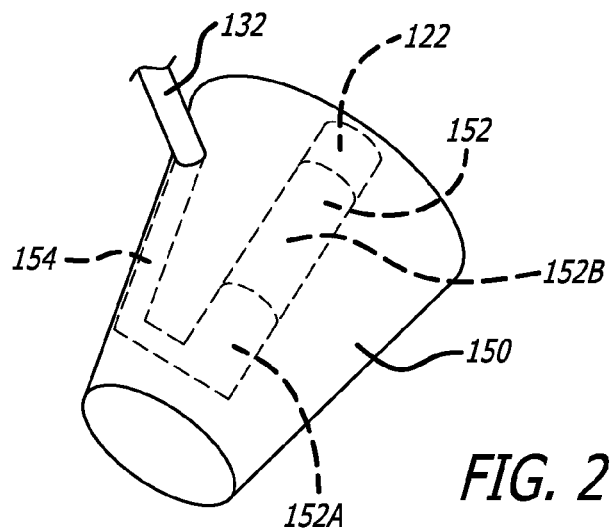
FIG. 2 is a perspective view of an embodiment of the stopcock device of the present disclosure as a first chamber is being filled.

According to other embodiments and as shown in FIG. 2, second chamber 152 comprises flow material reservoir 152A and a pressurized reservoir 152B separated by a flexible or movable separator, such as an elastomeric membrane or piston. As flow material reservoir is charged, the membrane or piston stretches or moves, thereby compressing gas in the pressurized reservoir. The same gas in pressurized reservoir is used as the gas from which second pressure sensor 122 takes measurements.

Second pressure sensor 122 is disposed to be in gaseous communication with second chamber 152. For example, second pressure sensor 122 is disposed immediately adjacent to second chamber 152, as shown in FIG. 1. According to alternative embodiments, second pressure sensor 122 is separated from second chamber 152 by a pressure sensing conduit.

According to embodiments, dispensing conduit 134 serves as a conduit from second chamber 152 to a target, for example a patient, where the flow material is intended. According to embodiments, flow regulator 160 may be disposed to modulate flow rate. Flow regulator 160 comprises flow restrictors, for example.

According to embodiments where it is used, a pressure sensing conduit serves as a conduit between second pressure sensor 122 and second chamber 152 when stopcock 150 is positioned so as to be in gaseous communication with pressure sensing conduit. According to embodiments, pressure sensing conduit comprises a small cavity having a pressure sensor; according to other embodiments, pressure sensing conduit comprises a tube, pipe, or other conduit with second pressure sensor 122 disposed somewhere therein to measure the pressure. In all cases, the total volume of second chamber 152, second chamber conduit 154, and pressure sensing conduit is a known volume.

Positioning device 158 connects to stopcock 150 and effects repositioning of stopcock 150. According to embodiments, positioning device 158 is a motor that rotates stopcock 150. According to embodiments, positioning device 158 may also be a device that moves a slideable stopcock back and forth.

According to embodiments, stopcock 150 occupies one of three positions: a fill position (FIG. 3) where second chamber 152 is in fluid communication with first chamber 110, but not in communication with dispensing conduit 134; a closed position (FIG. 4) where second chamber 152 it is not in fluid communication with either first chamber 110 or dispensing conduit 134; and a dispense position (FIG. 5) where second chamber 152 is in fluid communication with dispensing conduit 134, but not first chamber 110 and in which second pressure sensor 122 is in gaseous communication with second chamber 152.

Figure 3:
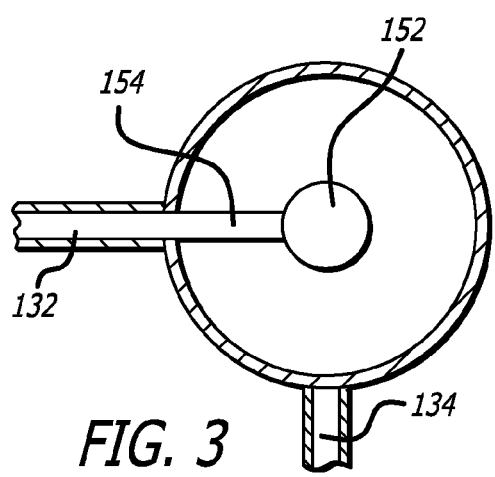
FIG. 3 is a cross-sectional view of an embodiment of the stopcock of the present disclosure as a second chamber is filled with a flow material.
Figure 4:
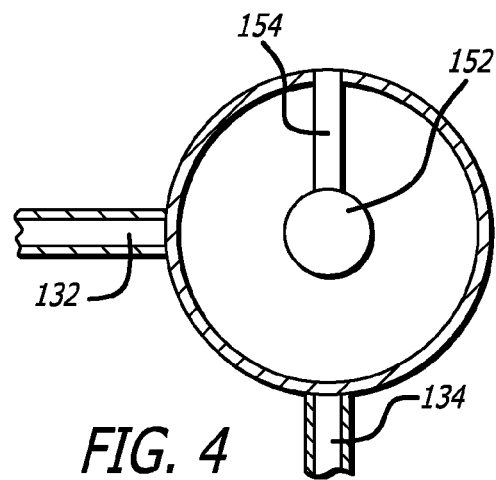
FIG. 4 is a cross-sectional view of an embodiment of a stopcock of the present disclosure in a closed position.
Figure 5:
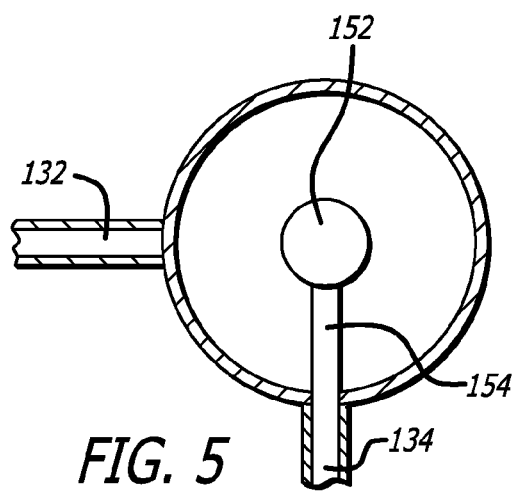
FIG. 5 is a cross-sectional view of an embodiment of a stopcock of the present disclosure in a dispensing position whereby flow material is dispensed.

According to embodiments and as illustrated in FIGS. 3-5, when stopcock 150 is in a fill position (FIG. 3), an aliquot of flow material is moved from first chamber 110 into second chamber 152, wherein second chamber 152 is filled with a flow material. Once filled, flow material is ready to be dispensed to a target, according to embodiments.

After second chamber 152 is filled with an aliquot of flow material, stopcock 150 is positioned in a closed position (FIG. 4) wherein second chamber 152 is sealed. According to embodiments, the pressure is measured in first chamber 110 or second chamber 152 to determine the volume of the aliquot transferred from first chamber 110 to second chamber 152. Artisans will note that pressure cannot be sensed for first chamber while first chamber 110 and second chamber 152 are in fluid or gas communication.

When stopcock 150 is positioned in a closed or dispensing position (FIGS. 4 and 5), second chamber 152 is in gaseous communication with second pressure sensor 122, but not with first chamber 110. In these positions, the pressure of the gas in second chamber 152 is sensed with second pressure sensor 122. The total volume of second chamber 152 is known, thereby allowing the amount of flow material dispensed or remaining in second chamber 152 to be calculated based on the change in pressure of second chamber 152.

According to embodiments, after filling second chamber 152 with an aliquot of flow material or after dispensing flow material, stopcock 150 is positioned in the closed position, the pressure is measured, and the flow material volume calculated (because the total volume of second chamber 152 when stopcock 150 is in the pressure sensing position is known).

To dispense flow material, stopcock 150 is positioned in its dispense position (FIG. 5) for a period of time. According to embodiments, stopcock 150 is then rotated to the closed position (FIG. 4) for a period of time that is used to measure the pressure.

According to embodiments, pressure measurements are taken in the dispense position (FIG. 5) to determine the flow rate in about real time without changing the position of stopcock 150. Because the volume of the aliquot of flow material that filled second chamber 152 is calculated from the pressure in first chamber 110 or second chamber 152, and because the total volume and initial values for the pressure of second chamber 152 are known, according to embodiments, stopcock need not be positioned in the closed position prior to dispensing the flow material, according to embodiments.

According to alternate embodiments, stopcock 150 occupies one of four positions: a fill position (FIG. 3) wherein second chamber 152 is in fluid communication with first chamber 110, but not in communication with dispensing conduit 134; a closed position (FIG. 4) where second chamber 152 is not in fluid communication with either first chamber 110 or dispensing conduit 134; a pressure sensing position, wherein second chamber 152 is in gaseous communication with second pressure sensor 122 and the pressure of second chamber may be measured; and a dispense position where second chamber 152 is in fluid communication with dispensing conduit 134, but not first chamber 110.

Figure 6:
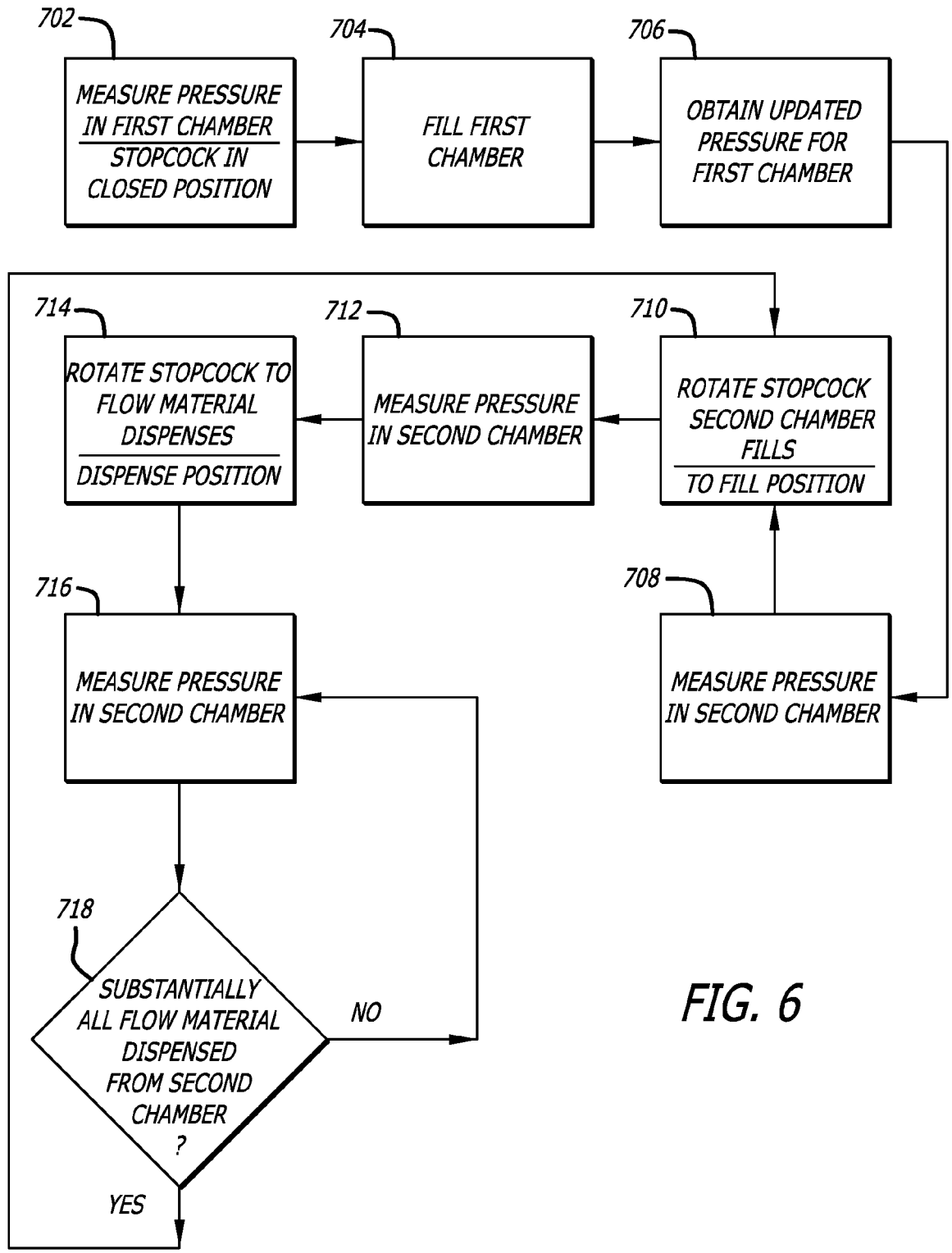
FIG. 6 is a flow diagram of an embodiments of a method for dispensing flow materials using the stopcock device of the present disclosure.

According to embodiments and as illustrated in FIG. 6, a method is disclosed for effecting flow of flow material from a source and through stopcock device 100. During the fill operation, according to embodiments, stopcock 150 is initially positioned into the closed position (FIG. 4), wherein it is not in fluid communication with either first chamber 110 or second chamber 152. In this position, an initial pressure measurement of first chamber 110 is made in operation 702. According to alternate embodiments, no initialization is necessary as the system will be in a known state prior to filling (for example, known volume of flow material in first chamber 110 and known initial volume of first chamber 110). In operation 704, first chamber 110 is filled with flow material to a desired level and a second pressure measurement is taken in operation 706, from which the total amount of flow material in first chamber 110 is calculated. After charging first chamber 110 with flow material, fill conduit 130 is closed and substantially sealed.

According to embodiments, the filling of first chamber 110 may be omitted where the device comprises a disposable that is discarded when the flow material in first chamber is spent.

In operation 704, according to embodiments, flow material enters through fill conduit 130 and into first chamber 110.

Flow of flow material into first chamber 110 via fill conduit 130 may be effected from any conventional pump, including specialized infusion pumps, for example those disclosed in U.S. Pat. Nos. 7,008,403; 7,341,581; and 7,374,556, which are hereby incorporated by reference in their entirety. As flow material enters first chamber 110, compressible member 112 or gas is compressed. Thus, compressible member 112 or the gas stores the energy that will later be used to effect movement of an aliquot of flow material from first chamber 110 to second chamber 152.

After first chamber 110 is filled, flow material is ready to be dispensed from first chamber 110 to second chamber 152. Prior to filling second chamber 152 with and aliquot of flow material, an initial pressure measurement of second chamber 152 is taken, according to embodiments in operation 708.

Stopcock 150 is positioned into the fill position in operation 710, whereby flow material flows from first chamber 110, through first chamber/stopcock conduit 132 and second chamber conduit 154, and into second chamber 152. As flow material enters into first chamber 110, it compresses compressible member, according to various embodiments. According to embodiments, only a small aliquot of flow material moves from first chamber 110 into second chamber 152 as second chamber 152 charges. For example, first chamber 110 may have a volume of 3 ml and second chamber 152 may have a volume of 0.3 ml. The small aliquot of flow material transferred is the max amount of flow material that can be inadvertently delivered in the event of an error.

After second chamber 152 is charged with flow material, the pressure of second chamber 152 is measured in operation 712. The volume of the aliquot transferred to second chamber may be calculated either from the change in pressure from first chamber 110 or by measuring the change in pressure in second chamber 152. For example, first pressure sensor 120 again measures the pressure of first chamber 110. Because flow material has been removed from first chamber 110 into second chamber 152, the volume of compressible member 112 or the gas is increased, thereby reducing the pressure. Thus, because the total volume of first chamber 110 is known, the amount of flow material transferred to second chamber 152 may be calculated, as shown below. Similarly, the volume of the aliquot of flow material in second chamber 152 may be calculated from the difference in pressure in second chamber measured before the aliquot of flow material is transferred and after the aliquot of flow material is transferred to second chamber 152. According to embodiments, both calculations may be used and an average value taken.

Once the volume of flow material in second chamber 152 is known, according to embodiments, stopcock 150 is positioned in its dispense position in operation 714. Because second chamber 152 also has disposed therein compressible member 112 or gas that is pressurized, flow material in second chamber 152 is dispensed due to the pressure exerted on it by compressible member 112 or the gas. According to embodiments, dispensing conduit 134 has disposed therein flow regulator 160, which is, for example, a flow restrictor or clamping device designed to regulate the flow rate of flow material.

Second pressure sensor 122, according to embodiments, measures the change in pressure as flow material is dispensed in operation 716. According to embodiments in which stopcock 150 has a pressure sensing position, stopcock 150 is alternated between a dispensing position (FIG. 5) and a pressure sensing position to determine the volume of flow material that has been dispensed. According to embodiments in which stopcock does not have a pressure sensing position, the pressure changes are sensed in real time in the dispense position (FIG. 5). Thus, the pressure change of the gas in second chamber 152 is gradual and predictable, allowing for a flow rate to be calculated. Because the volume of second chamber 152 is known, the rate of flow may be calculated, as shown below.

According to embodiments, the aliquot of flow material in second chamber 152 is small enough that determination of the flow from second chamber 152 is not required. In other words, because the aliquot size is so small, a flow rate with an acceptable level of error may be determined from the number of aliquots delivered over a period of time.

According to embodiments, gas from first chamber 110 and second chamber 152 is not dispensed with the flow material. Thus, the number of gas molecules in each respective chamber remains constant, as is required for the exemplary equations below to be true. Artisans will readily appreciate that these exemplary equations illustrate the principles by which the volume of flow material dispensed is calculated.

According to embodiments, stopcock device 100 is configured as an accessory to other pump devices whereby sterility of the flow material is maintained, but volumes of flow material are determined in about real time accurately.

For example, the present disclosure is provided as an accessory to infusion pumps. The pumps may be conventional or nonconventional pumping devices. Specialized pumps may also be used, including those with two, three, or more chambers, for example as disclosed in U.S. Pat. Nos. 7,008,403; 7,341,581; and 7,374,556, and U.S. Utility patent application Ser. Nos. 11/744,819 filed May 4, 2007 and 12/020,498, filed Jan. 25, 2008 (the contents of each above listed patent and patent application are incorporated by reference). Indeed, the devices of the present disclosure may be provided as accessories for pumps that are able to measure flow rate in about real time.

The devices of the present disclosure are also useful as safety devices for any pump, whereby upon an error state the maximum flow material that can be delivered to a patient upon a given error state is the small volume contained in second chamber 152 at the time of the error.

Figure 7:
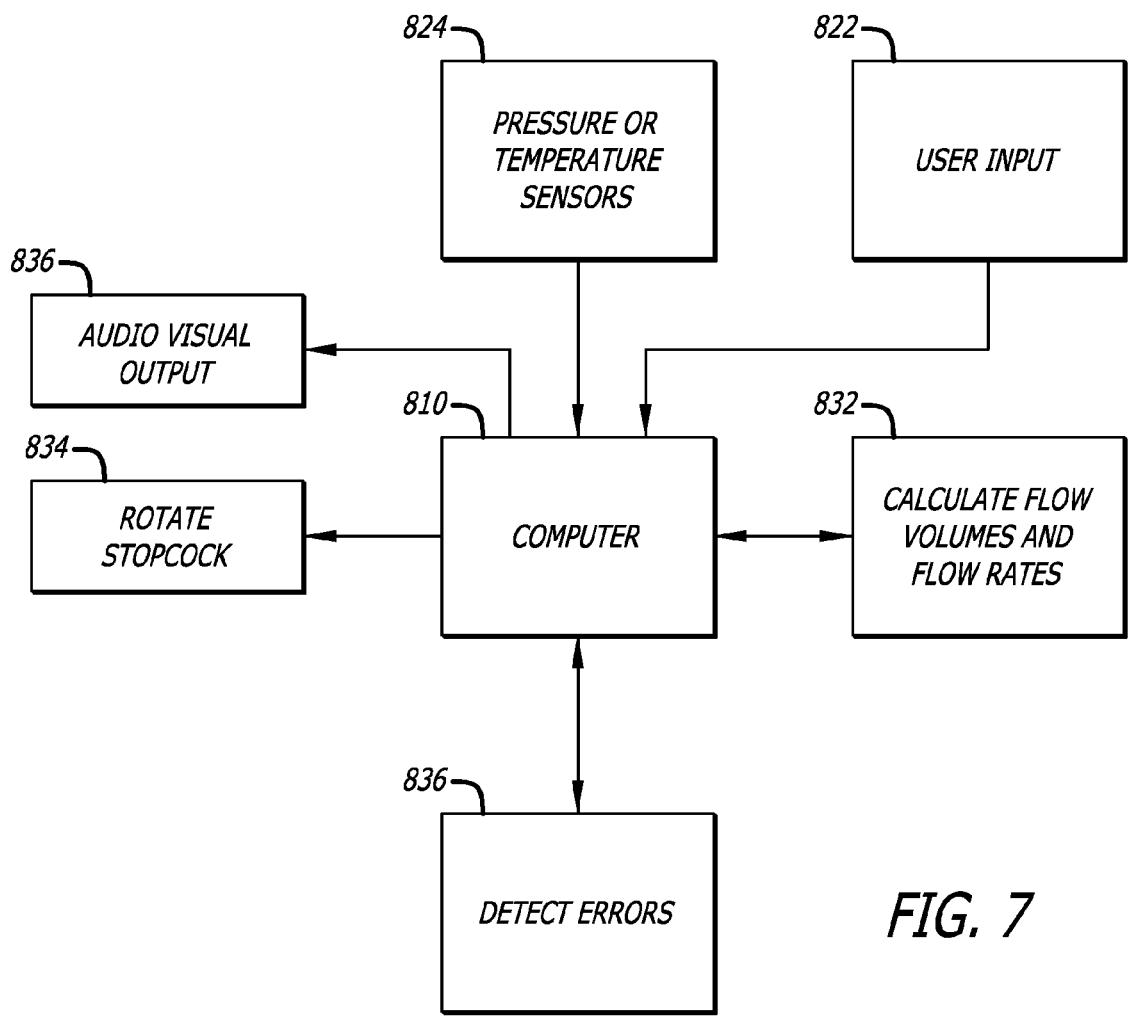
FIG. 7 is a block diagram of an embodiment of a processing system of the present disclosure.

According to embodiments and as illustrated in FIG. 7, stopcock device 100 also comprises computer 810 for controlling and performing the functions disclosed herein. Computer may be any computer that is capable of being configured to receive input from users 822 or pressure sensors or temperature sensors 824. Computer also calculates flow volumes and flow rates 832, checks for and detects error states 836, and repositions stopcock 834, and output audiovisual content 836.

According to embodiments, the ideal gas law is used to calculate the dispensed volumes of flow material. Generally, the ideal gas law is expressed as:

$$PV = nRT$$

where P is the pressure of the gas in the chamber, V is the volume of the chamber, T is the temperature of the chamber, n is the number of moles of gas, and R is the universal gas constant.

According to embodiments, first chamber 110 is of known total volume, containing a volume of gas. Similarly, second chamber 152 is of known total volume, containing a volume of gas. As disclosed earlier, first and second chambers 110, 152 may not have gas according to some embodiments, but other mechanical devices such as closed cell foam having therein a known volume of gas and a known compression profile, whereby the pressure readings of first chamber 110 are useful for the purposes of calculating a volume of flow material held in first chamber 110. The following exemplary calculations may be adapted for such embodiments without undue experimentation.

According to embodiments, because the total volume of first chamber 110 is known, the volume of flow material filling first chamber 110, as well as the volume of aliquots of flow material dispensed into second chamber 152 may be calculated. Likewise, because the total volume of second chamber 152 is known, the volume of flow material dispensed out of stopcock device 100 may be calculated. The exemplary calculations illustrate an embodiment whereby the volume of flow material dispensed is calculated.

Assuming constant temperature, the initial pressure of first chamber 110 is known or measured using first pressure sensor 120. Additionally, the total volume of first chamber 110 ($V_1$) and second chamber 152 ($V_2$) are known. Accordingly, an initial volume of flow material is placed in first chamber 110, thereby increasing the pressure of first chamber 110. The amount of flow material in first chamber 110 ($V_{FlowMaterial}$) is calculated:

$$P_{1empty}V_{1empty} = P_{1Filled}V_{1Filled}$$

$$V_{1Filled} = \frac{P_{1empty}V_{1empty}}{P_{1Filled}}$$

$$V_{FlowMaterial} = V_{1empty} - V_{1Filled}$$

where the volumes here measuring the initial and final gas volume, not flow material volume. If first chamber 110 is empty, then $V_{1Initial} = V_1$. Otherwise, the computer will keep track of the initial volume of first chamber 110 for each successive aliquot.

According to embodiments, where closed cell foam is placed in first chamber 110, the calculation for pressure will account for the physical characteristics imparted by compression of the foam, as well. After filling first chamber 110 with a flow material and calculating the volume of flow material that is in first chamber 110, fill conduit 130 is sealed.

Flow material may then flow from first chamber 110 to second chamber 152. According to embodiments, stopcock 150 is rotated whereby it is in its fill position, as illustrated in FIG. 3. The pressure within first chamber 110 causes flow material to move from first chamber 110 to second chamber 152, according to embodiments. According to other embodiments, gravity or mechanical devices can effect flow material movement from first chamber 110 to second chamber 152. The volume ($V_{Aliquot}$) of flow material that fills second chamber is calculated:

$$P_{1Initial}V_{1Initial} = P_{1Flowed}V_{1Flowed}$$

$$V_{1Flowed} = \frac{P_{1Initial}V_{1Initial}}{P_{1Flowed}}$$

$$V_{Aliquot} = V_{1Initial} - V_{1Flowed}$$

After second chamber is charged with an aliquot of flow material, stopcock is changed from its fill position (illustrated in FIG. 3) to another position, for dispensing, pressure measurement, or closed for accurate measurement of the pressure in first chamber 110.

To determine an amount of flow material dispensed at a given point, according to embodiments, similar calculation are performed for second chamber 152 to determine the amount of flow material dispensed. The gas volume of second chamber 152 after having receiving an aliquot is first determined:

$$P_{2Initial}V_{2Initial} = P_{2Filled}V_{2Filled}$$

$$V_{2Filled} = \frac{P_{2Initial}V_{2Initial}}{P_{2Filled}} \text{ or } V_{2Filled} = V_{2Initial} - V_{Aliquot}$$

When stopcock 150 is positioned in its dispense position, flow material is dispensed from stopcock 150 by virtue of the pressure within second chamber 152, gravity, or other mechanical forces, according to embodiments. Accordingly, as flow material is dispensed out of second chamber 152, the volume dispensed is calculated. The dispensed flow material volume is determined exactly opposite of the method by which the volume filled into first chamber 110 is calculated, according to embodiments. For example:

$$P_{2Filled}V_{2Filled} = P_{2Dispensed}V_{2Dispensed}$$

$$V_{2Dispensed} = \frac{P_{2Filled}V_{2Filled}}{P_{2Dispensed}}$$

$$V_{Dispensed} = V_{2Filled} - V_{2Dispensed}$$

According to embodiments, stopcock 150 is alternated between its dispense position and its pressure sensing position to make pressure measurements. According to other embodiments, stopcock 150 remains in its dispense position and the pressure of second chamber 152 is periodically assayed to determine the volume of flow material dispensed.

A shortened version of the equations follows, where it isn't necessary to determine the gas volume in second chamber 152.

$$V_{Dispensed} = V_{2Filled} - V_{2Dispensed}$$

$$V_{Dispensed} = V_{2Filled} - \frac{P_{2Filled}V_{2Filled}}{P_{2Dispensed}}$$

$$V_{Dispensed} = \frac{P_{2Dispensed}V_{2Filled}}{P_{2Dispensed}} - \frac{P_{2Filled}V_{2Filled}}{P_{2Dispensed}}$$

$$V_{Dispensed} = \frac{V_{2Filled}(P_{2Dispensed} - P_{2Filled})}{P_{2Dispensed}}$$

$$V_{Dispensed} = \frac{V_{2Filled}}{P_{2Dispensed}}\Delta P_2$$

$$V_{Dispensed} = \frac{V_2 - V_{Aliqout}}{P_{2Dispensed}}\Delta P_2.$$

According to embodiments, temperature sensors may be disposed in substantially the same locations as each pressure sensor to improve the accuracy of the calculations. The application of temperature into the exemplary calculation shown below are will within the skill and understanding of a person of ordinary skill in the art.

According to embodiments, the above equations are adaptable to a single pressure sensor 122 in second chamber 152. Such a configuration is possible when knowing the initial volume in first chamber 110 is not necessary or desirable, or when the volume of first chamber 110 is known, for example when the device disclosed herein is a disposable. According, only the volume of each aliquot of flow material is calculated by measuring the pressure differentials in the second chamber 152. For example, the volume of each aliquot ($P_{2Filled}$) may be calculated independent of any calculations related to first chamber 110:

$$P_{2Initial} V_{2Initial} = P_{2Filled} V_{2Filled}$$

$$V_{2Filled} = \frac{P_{2Initial} V_{2Initial}}{P_{2Filled}}.$$

Knowing the $P_{2Filled}$ value allows for the calculation of the dispensed volume as disclosed above.

According to embodiments, because stopcock 150 eliminates direct fluid communication between the pump and the target of the flow material, it provides a safety mechanism for the pump. If a malfunction of the pump or stopcock device 100 occurs, the maximum unintended amount of flow material that can possibly be dispensed to the target is the small aliquot in second chamber 152. In certain applications, for example in the delivery of insulin, these types of safety mechanisms are important for preventing unintended delivery of insulin due to malfunction.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A flow regulating device comprising:
   a first chamber;
     a first compressible member configured to store energy disposed in the first chamber;
     a stopcock;
     a second chamber disposed inside the stopcock for holding flow material to be dispensed;
     a second compressible member configured to store energy disposed in the second chamber;
     a first chamber/stopcock conduit disposed between the first chamber and the stopcock to provide fluid communication therebetween;
   a first pressure sensor in communication with the first chamber; and
     wherein the second chamber is filled with flow material from first chamber when stopcock is in a first position and the stopcock device only dispenses flow material when the stopcock is in the second position that is not in fluid communication with the first chamber.

2. The device of claim 1, further comprising a second pressure sensor disposed in communication with the second chamber.

3. The device of claim 1, wherein the first pressure sensor is in communication with the second chamber.

4. The device of claim 1, wherein the first compressible member and second compressible member each comprise at least one of a closed cell foam, a piston, or a elastomeric diaphragm that segregates gas from the flow material.

5. The device of claim 1, further comprising a motor connected to the stopcock wherein the stopcock is rotatable between the first position and the second position with the motor.

6. The device of claim 1, wherein the stopcock occupies one of three positions comprising:
   a fill position in which the second chamber is in fluid communication with the first chamber for filling the second chamber with flow material from the first chamber,
   a dispense position in which the second chamber is in fluid communication with a dispensing conduit, but not with the first chamber, and
   a closed position wherein the second chamber is not in fluid communication with the first chamber or the dispensing conduit.

7. The device of claim 2, wherein the stopcock occupies one of four positions comprising:
   a fill position with the second chamber in fluid communication with the first chamber for filling the second chamber with flow material from the first chamber,
   a dispense position with the second chamber in fluid communication with a dispensing conduit but not in fluid communication with the first chamber for dispensing flow material from the second chamber,
   a pressure sensing position with the second chamber in communication with the second pressure sensor for measuring a gas pressure in the second chamber, and
   a closed position wherein the second chamber is not in fluid communication with the first chamber or the dispensing conduit.

8. The device of claim 2, wherein the first pressure sensor and the second pressure sensor are configured to measure pressures in the first chamber and second chamber, respectively, to assist determining a volume of flow material dispensed.

9. The device of claim 8, wherein the device is configured to determine the volume of flow material dispensed in about real time.

* * * * *